(12) United States Patent
Akintelure et al.

(10) Patent No.: US 12,029,803 B2
(45) Date of Patent: ***Jul. 9, 2024

(54) PERSONAL CLEANSING COMPOSITIONS, METHODS AND USES

(71) Applicant: The Procter & Gamble Company, Cincinnati, OH (US)

(72) Inventors: Olubolaji Akintelure, Mason, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,068

(22) Filed: Jun. 7, 2022

(65) Prior Publication Data

US 2022/0401332 A1    Dec. 22, 2022

Related U.S. Application Data

(60) Provisional application No. 63/211,176, filed on Jun. 16, 2021.

(51) Int. Cl.
| | |
|---|---|
| *A61K 8/00* | (2006.01) |
| *A61K 8/04* | (2006.01) |
| *A61K 8/06* | (2006.01) |
| *A61K 8/33* | (2006.01) |
| *A61K 8/34* | (2006.01) |
| *A61K 8/365* | (2006.01) |
| *A61K 8/44* | (2006.01) |
| *A61K 8/46* | (2006.01) |

(Continued)

(52) U.S. Cl.
CPC ............. *A61K 8/463* (2013.01); *A61K 8/042* (2013.01); *A61K 8/068* (2013.01); *A61K 8/33* (2013.01); *A61K 8/345* (2013.01); *A61K 8/365* (2013.01); *A61K 8/442* (2013.01); *A61Q 19/10* (2013.01); *A61K 2800/33* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 3,480,556 | A | 11/1969 | Witt et al. |
| 4,441,881 | A | 4/1984 | Ruppert et al. |
| 6,060,443 | A | 5/2000 | Cripe |

(Continued)

FOREIGN PATENT DOCUMENTS

| | | |
|---|---|---|
| CA | 2271200 A1 | 6/1998 |
| EP | 0439316 A2 | 7/1991 |

(Continued)

OTHER PUBLICATIONS

All Office Actions; U.S. Appl. No. 17/337,493, filed Jun. 3, 2021.

(Continued)

*Primary Examiner* — Necholus Ogden, Jr.
(74) *Attorney, Agent, or Firm* — Alexandra S. Anoff

(57) ABSTRACT

Described herein, personal cleansing compositions, methods and uses. Personal cleansing compositions can include a surfactant, a perfume, a hydric solvent, and water, wherein the composition is structured.

20 Claims, 10 Drawing Sheets

(51) Int. Cl.
 *A61Q 19/10* (2006.01)
 *C11D 1/00* (2006.01)

(56) References Cited

U.S. PATENT DOCUMENTS

| | | |
|---|---|---|
| 6,228,829 B1 | 5/2001 | Vinson et al. |
| 7,439,403 B2 | 10/2008 | Holscher |
| 9,493,725 B2 | 11/2016 | Vinson et al. |
| 9,493,726 B2 | 11/2016 | Vinson et al. |
| 10,441,519 B2 | 10/2019 | Zhao et al. |
| 2002/0022583 A1 | 2/2002 | Buzzaccarini et al. |
| 2003/0216278 A1 | 11/2003 | Depoot et al. |
| 2016/0068784 A1 | 3/2016 | Vinson et al. |
| 2016/0068785 A1 | 3/2016 | Vinson et al. |
| 2017/0137747 A1 | 5/2017 | Tang |
| 2017/0175058 A1 | 6/2017 | Depoot |
| 2017/0253839 A1 | 9/2017 | Scheibel |
| 2018/0110697 A1 | 4/2018 | Smith, III |
| 2019/0117544 A1* | 4/2019 | Zhao ................. A61Q 5/02 |
| 2020/0283705 A1 | 9/2020 | Smets |
| 2020/0407665 A1 | 12/2020 | Joos |
| 2021/0380902 A1 | 12/2021 | Vinson et al. |
| 2022/0064569 A1 | 3/2022 | Vinson et al. |
| 2023/0174894 A1 | 6/2023 | Stenger |
| 2023/0174896 A1 | 6/2023 | Stenger et al. |
| 2023/0174901 A1 | 6/2023 | Stenger et al. |

FOREIGN PATENT DOCUMENTS

| | | |
|---|---|---|
| GB | 2208516 A | 4/1989 |
| JP | 2010013579 A | 1/2010 |
| WO | 9823566 A1 | 6/1998 |
| WO | 2007064525 A1 | 6/2007 |
| WO | 2013000571 A1 | 1/2013 |
| WO | 2016040241 A1 | 3/2016 |
| WO | 2016040248 A2 | 3/2016 |
| WO | 2019055256 A1 | 3/2019 |
| WO | 2021247801 A1 | 12/2021 |

OTHER PUBLICATIONS

All Office Actions; U.S. Appl. No. 17/339,004, filed Jun. 4, 2021.
PCT Search Report and Written Opinion for PCT/US2022/033547 dated Jan. 4, 2023, 12 pages.
All Office Actions; U.S. Appl. No. 18/390,735, filed Dec. 20, 2023.
U.S. Unpublished U.S. Appl. No. 18/390,735, filed Dec. 20, 2023, to Phillip Kyle Vinson et al.

* cited by examiner

PERSONAL CLEANSING COMPOSITIONS, METHODS AND USES

FIELD OF THE INVENTION

The present application generally relates to personal cleansing composition, its methods and its uses. The personal cleansing composition includes a surfactant comprising a specific C13 alkyl sulfate anionic surfactant and a cosurfactant, perfume, hydric solvent and water. At least a portion of the composition is in a lamellar phase.

BACKGROUND OF THE INVENTION

Cleansing is an activity that has been done for hundreds of years. Early cleansers were based on either soap chemistry or simple mechanical action in order to remove dirt from the skin, as well as endogenous soils such as sweat, sebum, and body odors. Smelling clean is an important benefit, however, early on, perfume was applied after cleansing as early cleansers were not designed to deposit a consumer preferred amount of perfume on skin. So, the inclusion of large amounts of perfume in a cleansing composition was both wasteful, as it was washed down the drain, and expensive. As skin cleansing compositions have become more complex, providing scent during cleansing and residual scent on the skin after cleansing are expected by users of modern skin cleansers. Personal cleansing compositions comprising sodium trideceth-2 sulfate and a hydric solvent were explored to provide microemulsion phases to deliver fragrance.

Ethoxylated surfactants such as Sodium Laureth Sulfate (SLES or SLE3S) or Sodium Trideceth-n Sulfate (STnS) are used widely across the cosmetic industry in personal cleansing products. These surfactants traditionally have been used to achieve a consumer desirable product profile which includes dispensed viscosity/product texture, lather, cleaning, and deposition of hair/scalp actives. Ethoxylation provides enhanced solubility, reduced crystallization in liquids, enhanced polymer interaction for coacervate formation and subsequent benefit delivery to the skin and scalp, increased mildness to the skin, and improved quality of lather.

Alkoxylated fatty alcohols are used are in many industries. For example, they can be used as non-ionic surfactants in detergents and cleansers. They can also be an intermediate in the production of other surfactants through processes like sulfation. Current sulfation processes of alkoxylated fatty alcohols can result in the formation of unwanted contaminants such as dioxane components which can remain as part of the alkoxylated fatty alcohol sulfate as it is sold or used. Such unwanted contaminants can be removed by additional treatment processes, e.g. a relatively and costly vacuum stripping process.

As such, there is a desire to make personal cleansing compositions that contain relatively very low amount or no ethoxylated surfactants, to mitigate any undesired contaminant profile and any need of any additional treatment processes.

There is a need to develop a formulation approach for personal cleansing compositions that utilize relatively very low or non-ethoxylated surfactants, without having negative consumer noticeable trade-off's.

There is still a need to provide personal cleansing compositions with relatively very low ethoxylated or non-ethoxylated surfactants which can provide similar or improved scent during cleansing and/or residual scent on the skin are desired, in compositions which retain their effectiveness in cleansing and are easy to dispense and spread on the skin.

SUMMARY OF THE INVENTION

A personal cleansing composition is provided and comprises: (i) from about 30% to about 50%, preferably from about 32% to about 45%, more preferably from about 35% to about 40% by weight of the composition, of a surfactant, wherein the surfactant comprises a C13 alkyl sulfate anionic surfactant and a cosurfactant, wherein the C13 alkyl sulfate anionic surfactant consists of: (a) less than about 40% by weight of the C13 alkyl sulfate anionic surfactant of a linear C13 alkyl sulfate, and (b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and (c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant;
(ii) from about 4.5% to about 25%, preferably from about 7% to about 22%, more preferably from about 8% to about 20%, by weight of the composition, of a perfume;
(iii) from about 3% to about 15%, preferably from about 4% to about 13%, more preferably from about 5% to about 11%, by weight of the composition, of a hydric solvent; and (iv) water. The personal cleansing composition is structured, preferably at least a portion of the composition is in a lamellar phase.

Alternatively, a personal cleansing composition is provided and comprises: (i) a surfactant, wherein the surfactant comprises a C13 alkyl sulfate anionic surfactant and a cosurfactant, wherein the C13 alkyl sulfate anionic surfactant consists of: (a) less than about 40% by weight of the C13 alkyl sulfate anionic surfactant of a linear C13 alkyl sulfate, and (b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and (c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant;
(ii) a perfume at a weight ratio perfume:surfactant of at least about 1:10; (iii) a hydric solvent at a weight ratio hydric solvent:surfactant of at least about 2:9; (iv) between about 25% to about 50% water by weight of the composition; wherein the personal cleansing composition has an elastic modulus G' at 1 Hz from about 70 Pa to about 2500 Pa according to the G' and G" Test Method as disclosed herein.

A method of providing similar or enhanced in-vitro bloom or fragrance skin deposition of a rinse-off microemulsion cleansing composition, is provided and comprises, a synergistic combination of a C13 alkyl sulfate anionic surfactant and a hydric solvent, including: (i) from about 30% to about 50%, preferably from about 32% to about 45%, more preferably from about 35% to about 40% by weight of the composition, of a surfactant, wherein the surfactant comprises a C13 alkyl sulfate anionic surfactant and a cosurfactant, wherein the C13 alkyl sulfate anionic surfactant consists of: (a) less than about 40% by weight of the C13 alkyl sulfate anionic surfactant of a linear C13 alkyl sulfate, and (b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant; and (c) less than about 5% by weight of other branched C13 alkyl sulfate anionic surfactant, wherein (a), (b) and (c) add up to about 100% by weight of the C13 alkyl sulfate anionic surfactant; (ii) from about 4.5% to about 25%, preferably from about 7% to about 22%, more preferably from about 8% to about 20%, by weight of the composition, of a perfume; (iii) from about 3% to about 15%, preferably from about 4% to about 13%, more preferably from about 5% to about 11%, by weight of the composition, of a hydric solvent; and (iv) water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

Use of a C13 alkyl sulfate anionic surfactant for providing a stable or improved stable gel of a personal cleansing composition, as described hereinbefore.

Use of a C13 alkyl sulfate anionic surfactant for providing an improved lather stability of a personal cleansing composition, as described hereinbefore.

Use of a C13 alkyl sulfate anionic surfactant for providing a similar or denser lather of a personal cleansing composition, as described hereinbefore.

Use of a C13 alkyl sulfate anionic surfactant and a hydric solvent to provide similar or enhance in-vitro bloom of a personal cleansing composition, as described hereinbefore.

Use of a C13 alkyl sulfate anionic surfactant and a hydric solvent to provide similar or enhance fragrance longevity on skin of a personal cleansing composition, as described hereinbefore.

Use of a C13 alkyl sulfate anionic surfactant and a hydric solvent to provide similar or enhance fragrance of a personal cleansing composition as described hereinbefore prior to use.

Use of a C13 alkyl sulfate anionic surfactant and a hydric solvent to provide similar or enhance fragrance on skin upon initial application of a personal cleansing composition as described hereinbefore.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions of Terms

Figure 1:
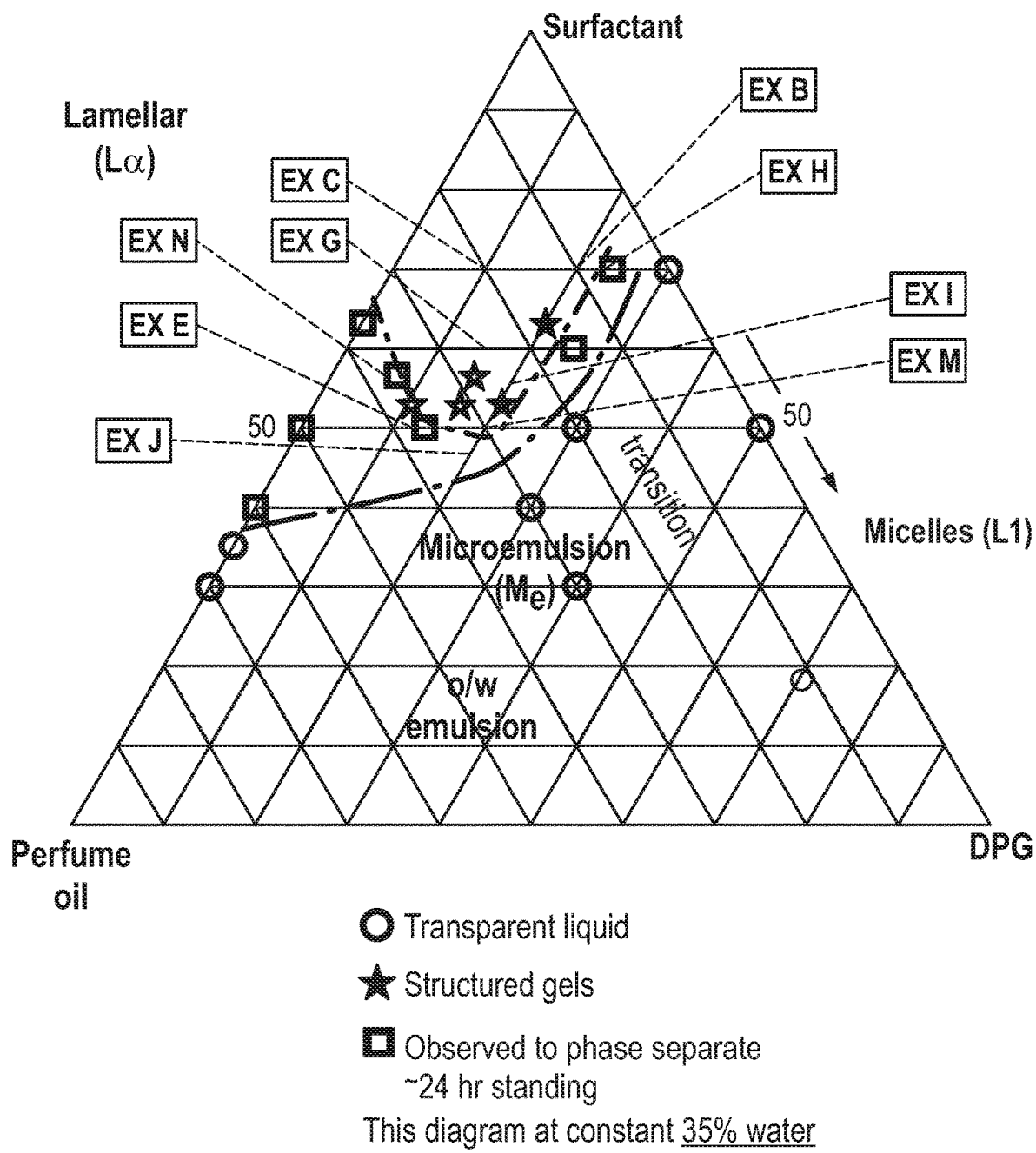
FIG. 1 is a ternary diagram at a constant water percentage of 35% by weight of the composition showing surfactant, dipropylene glycol (DPG), and perfume oil.

In this document, including in all embodiments of all aspects of the present invention, the following definitions apply unless specifically stated otherwise.

All percentages are by weight (w/w) of the composition, unless otherwise specified. "% wt." means percentage by weight. References to 'parts' e.g. a mixture of 1 part X and 3 parts Y, is a ratio by weight. All ratios or percentages are weight ratios or weight percentages unless specifically stated otherwise. An "active composition" is the composition absent water, and an "active ingredient" is the ingredient absent its water "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 25° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level and do not include carriers or by-products that may be included in commercially available materials.

Herein, "comprising" means that other steps and other ingredients can be in addition. "Comprising" encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "free of" as used herein means that the composition comprises 0% of an ingredient by total weight of the composition, thus no detectable amount of the stated ingredient.

The term "substantially free of" as used herein means less than about 1%, less than about 0.8%, less than about 0.5%, less than about 0.3%, or less than an immaterial amount of by total weight of the composition.

The term "cleansing composition" as used herein refers to compositions intended for topical application to the skin for cleansing.

The term "concentrate/concentrated" as used herein with respect to a cleansing composition refers to a composition where the weight percentage of a surfactant relative to the total composition is greater than about 15%.

The term "C13 alkyl sulfate anionic surfactant" refers to a sulfated anionic surfactant including an alkyl group having a total number of 13 carbon atom numbers.

The term "2-branched C13 alkyl sulfate anionic surfactant" as used herein refers to a C13 alkyl sulfate anionic surfactant having an alkyl chain positioned at carbon position 2.

The term "Other branched C13 alkyl sulfate anionic surfactant" as used herein refers to any other branched C13 alkyl sulfate anionic surfactants that are not a 2-branched C13 alkyl sulfate anionic surfactant, like 3-branched or 4-branched or 5-branched, etc., C13 alkyl sulfate anionic surfactant.

The term "gel" as used herein refers to a material or composition that does not flow under its own weight and has a G' greater than about 25 Pa at 1 Hz in an oscillatory rheology test.

The term "shelf stable gel" as used herein refers to a material or composition that does not flow under its own weight and has a G' from about 25 Pa to less than 70 at 1 Hz in an oscillatory rheology test.

The term "stable gel" as used herein refers to a material or composition that does not separate into more than one phase in a centrifuge test, is able to retain small air bubbles upon standing for 1 day at ambient conditions, and has a G' greater or equal than about 70 Pa at 1 Hz in an oscillatory rheology test.

The term "hydric solvent" as used herein refers to a solvent that is neutral organic species that contains at least 2 hydroxyl groups and is not a hydrotrope.

The term "hydrotrope" as used herein refers to a charged, amphiphilic solubility modifier. Hydrotropes are generally charged olefins especially an olefin sulfonate such as an aromatic sulfonate.

The term "relative bloom" as used herein refers to perfume in the headspace over a composition during use for a perfumed cleansing composition relative to concentration for a conventional, hydric solvent free, control micelle composition having 10 wt. % starting surfactant and 1 wt. % starting perfume when the same perfume is used in the composition and the micelle composition.

The term "in-vitro bloom" as used herein refers to the amount of perfume experienced at a weight ratio at least from 2:1 water to composition dilution versus the amount of perfume in the headspace prior to dilution and can be measured in accordance with Perfumed Headspace Abundance During Dilution Method set out below.

The term "micelle" as used herein refers to a structure comprising individual surfactant molecules aggregated to form a hydrophobic core region with externally facing polar head groups in equilibrium with surfactant monomers in a polar phase, having a characteristic dimension that is about two surfactant lengths, i.e., generally less than about 10 nm in diameter.

The term "microemulsion" as used herein refers to a thermodynamically stable isotropic mixture of oil, surfactant, and water comprising an interior hydrophobic core, having a diameter greater than about twice the extended length of the surfactant molecule, i.e., generally having at least one diameter dimension greater than about 3.5 nm diameter as measured by neutron scattering.

The term "mixtures" as used herein is meant to include a simple combination of materials and any compounds that may result from their combination The term "perfume" as used herein refers to a mixture of volatile organic oils having a pleasant aroma wherein the perfume components have individual molecular weights between about 75 and 400 Daltons.

The term "rinse-off" as used herein means the intended product usage includes application to skin followed by rinsing and/or wiping the product from the skin within a few seconds to minutes of the application step. The product is generally applied and rinsed in the same usage event, for example, a shower.

"Room temperature" refers to a temperature of 25° C.

The term "solvent" as used herein refers to species or mixture of species present in a molecular solution in the greatest molar concentration acting in a way to dissolve other species, the latter species generally being larger molecules.

The term "single phase" as used herein when used herein with respect to inventive cleansing compositions refers to homogeneity when measured at the designated temperature in accordance with the Centrifuge Test.

The term "structured" as used herein refers to a personal cleansing composition that may contain more than one phases that do not separate into two or more visible layers or phases in the centrifuge test as disclosed herein; and do not separate upon standing for 24 hr at ambient conditions.

The objects of the present invention are to provide personal cleansing products, methods and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

Chemical contaminants are sometimes found in raw materials or products utilizing raw materials. For example, 1,4-dioxane is an undesirable byproduct of detergent making. As an industrial processing solvent or chemical intermediate, 1,4-dioxane has previously been reported to be used in the production of products that may have commercial or consumer applications such as paints, adhesives, detergents, and pesticides. As such 1,4-dioxane may be present as a contaminant in consumer cosmetics/toiletries, household detergents, pharmaceuticals, foods, agricultural and veterinary products and ethylene glycol-based antifreeze coolants. It is formed as a reaction byproduct during the manufacturing of ethoxylated surfactants. Manufacturers can remove most of the 1,4-dioxane in consumer products through a vacuum stripping process or by improved methods of removing contaminants, like 1,4-dioxane from already ethoxylated surfactants.

However, there is a desire to make personal cleansing compositions that contain relatively very low amount or no ethoxylated surfactants, without having negative consumer noticeable trade-off's.

Initially, a non-ethoxylated surfactant, namely non-ethoxylated sodium tridecyl sulfate (ST0S) has been considered. However, the personal cleansing compositions did not appear to meet the gel stability properties in terms of rheology or did not provide any significant perfume delivery onto skin. The personal cleansing compositions comprising non-ethoxylated sodium tridecyl sulfate did not form lamellar phase and no acceptable microemulsion phases were also found.

To provide gel stability and high perfume delivery personal cleansing compositions, a specific surfactant structure needs to be found and optimized. Previously, the surfactant structure included the branched alkyl hydrocarbon chains, a hydrophilic ethoxylate spacer, and an anionic sulfate head group in combination with other ingredient components to produce personal cleansing compositions that organize into a lamellar phase that is desirable for dispensing rheology and aesthetics, and which are at the same time capable of diluting into a microemulsion in the presence of water.

The sodium trideceth-n hydrocarbon is a highly branched alkyl sulfate, and able to accomplish all these structure-related needs for high perfume delivery compositions, but in the absence of ethoxylation, inventors have found that it was unable to produce the abundance of multilamellar vesicles necessary to deliver desirable use aesthetics. Further, connected to these structural observations, non-ethoxylated sodium tridecyl sulfate that is highly branched was unable to produce a stable lamellar phase, and does not have the resulting elastic modulus, G' for useful product use aesthetics.

Surprisingly, inventors have discovered a new C13 alkyl sulfate anionic surfactant preferably a non-ethoxylated C13 alkyl sulfate anionic surfactant.

The C13 alkyl sulfate anionic surfactant consists of:
(a) less than about 40% by weight of the C13 alkyl sulfate anionic surfactant of a linear C13 alkyl sulfate, and (b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant, and (c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant.

Surprisingly, inventors have found by changing the nature and the distribution of the hydrocarbon branching of a 2-branched alkyl sulfate anionic surfactant, personal cleansing compositions comprising the C13 alkyl sulfate anionic surfactant as described herein are structured and may have especially a structured lamellar phase.

Personal cleansing compositions comprising the C13 alkyl sulfate anionic surfactant as described herein for a stable gel that has an elastic modulus G' as set out more in details hereinafter. The gel remains stable without any further additions of any ethoxylated anionic surfactants.

Preferably, at least a portion of the composition is in the lamellar phase

The resulting personal cleansing compositions may have a microemulsion phase even at low water content, i.e. without the need of any further dilution.

Also, the personal cleansing compositions may be further diluted into an increased microemulsion phase from a lamellar phase at low water content.

Personal cleansing compositions are easy to dispense and spread on the skin without running off.

To fit with current consumer habits during body cleansing, a personal cleansing composition can be in the form of a stable gel having a structure defined by an elastic modulus, G', a viscous modulus, G'', a viscosity, and a shear thinning viscosity ratio as measured by the test methods below. The gel may comprise a lamellar phase, proximal to a micelle composition. In some cases, when the gel has a relatively high perfume concentration in its headspace, it is believed to be in equilibrium with a microemulsion phase, since the gel can evince a characteristic lamellar x-ray diffraction pattern. In other cases, the gel can have a high perfume concentration in the headspace only after dilution water is introduced.

Inventors have found that when G' is below about 70 Pa, the personal cleansing compositions were not fully lamellar and tended to phase separate and become an unstable gel.

As a synergic combination between a surfactant comprising a C13 alkyl sulfate anionic surfactant as described herein and a hydric solvent such as dipropylene glycol, inventors have found that the combination of the C13 alkyl sulfate anionic surfactant and hydric solvent is unique in that it has a broad range over which it can help to create a microemulsion proximal to a lamellar phase in a personal cleansing composition.

FIG. 1 shows the phase diagram for a surfactant comprising a C13 alkyl sulfate anionic surfactant as defined hereinafter and a cosurfactant, preferably when the C13 alkyl sulfate anionic surfactant is combined with the cosurfactant from 10:1 to 4:1, such as 6.7:1 weight ratio as an example in FIG. 1; combined with a hydric solvent, e.g. dipropylene glycol (DPG) and a representative perfume oil fragrance.

The entirety of the diagram is at 35% water content, the points on the diagram thus constituting the non-water component of the personal cleansing composition. The personal cleansing composition forms a stable gel in the region designated 'Lamellar' above about 50% surfactant, below about 28% DPG and below about 36% fragrance. When more than about 28% DPG is used, the hydric solvent dissolves the lamellar structure and an additional phase forms, in the two-phase region between lamellar and micelles and between lamellar and microemulsion. A transition region may exist between micelles and microemulsion, which cannot be determined by visual observation or rheology measurements. When too much fragrance is used, the lamellar phase cannot dissolve all of it, and it becomes a second phase, which is less dense than the lamellar phase so it may be a microemulsion in equilibrium with the lamellar phase. When too little surfactant is used, lamellar phase does not form, as there is sufficient water and hydric solvent to allow the greater surfactant spacing.

Lather Benefits

Some personal cleansing compositions may form microemulsions but perform poorly for lathering and hence cleaning, which are important features for consumers. Personal cleansing compositions comprising the C13 alkyl sulfate anionic surfactant as described herein can also have consumer acceptable lather properties as evidenced in more details hereinafter.

Lather can be measured in accordance with the Cylinder Method described below. Compositions may have a lather volume of about 500 mL or more, preferably about 600 mL or more, more preferably from about 630 mL to about 1050 mL. Compositions may have a lather density of about 0.03 g/cc, about 0.04 g/cc, about 0.05 g/cc, 0.055 g/cc, 0.06 g/cc, 0.065 g/cc, or more. Compositions may have a lather mass of about 20 g, about 25 g, about 30 g, about 35 g, about 40 g, about 45 g, or more.

A denser lather is obtained for personal cleansing compositions comprising the C13 alkyl sulfate anionic surfactant as described herein, which is primarily a function of bubble elasticity resulting from improved packing at the interface compared to when the anionic surfactant is sodium trideceth-n sulfate (being either ST2S or ST3S).

Perfume-Related Benefits

Modern consumers of cleansing compositions expect the composition to provide scent both during use and to have residual scent on the skin after use, making perfume an important component of personal cleansing compositions. Perfume is also an important component of many personal cleansing compositions to mask the base odor of cleansing ingredients, which can be unpleasant.

Perfume is composed of mostly hydrophobic oil, whereas personal cleansing compositions generally have an aqueous, continuous phase which provides essentially no ability to carry perfume. It is desirable to provide perfume in a soluble form in a liquid cleansing composition since insoluble phases of any kind can lead to instability problems in the composition. Perfume is therefore generally solubilized within the surfactant component of personal cleansing compositions, such as micelles, lamellar structures, vesicles and the like. Surfactant structures of all kinds contain hydrophobic regions due to the aggregation of surfactant tails, which are able to solubilize significant quantities of perfume oil. Perfume generally exists within the surfactant tails as a molecular solution due to the interaction of the perfume with the surfactant tails, not as a colloidal structure such as an emulsion droplet, which is not thermodynamically stable.

A problem exists in providing perfume scent during use and residual scent to the skin from personal cleansing compositions. Well known physical laws govern the relationship between perfume in the air in equilibrium with perfume solubilized in a micelle or other environment. This relationship is defined by the mole fraction of perfume in the soluble environment, generally the micelle. Micelles are common features of skin cleansers since even non-micellar surfactant compositions generally become micelles during the dilution experienced while cleansing.

Since the perfume concentration in a personal cleansing composition is generally only 25% or less on a molar basis in the surfactant micelle, the vapor pressure of each perfume molecule can be reduced by 75% or even more, due to its solubilization in the micelle. The desire to deliver perfume to the skin suffers from a similar fate during cleansing. Perfume molecules can diffuse, or partition into the skin during cleansing. The driving force to do so is the thermodynamic activity coefficient gradient for the perfume molecules. While a pure perfume applied to the skin, having a high activity coefficient, can partition quickly into skin, perfume located in a surfactant micelle proximal to the skin suffers from an activity coefficient reduction (75% or more) due to micellar solubilization. Therefore most perfume in personal cleansing compositions (about 90%) generally is washed away during rinsing before it can partition into the skin or bloom into the headspace. The result is the skin retains no or very little scent and only for a short duration after a typical cleansing event. Thus, delivery of perfume to the air and to the skin during cleansing is inefficient and therefore expensive.

Overcoming these technical constraints in order to increase perfume delivery to the skin and the bloom of perfume during a cleansing event is not simply a matter of adjusting formula components at increased cost. Natural limits exist related to factors such as solubility. For example, increasing perfume in a personal cleansing composition is not only costly, but is also unfeasible considering the abundance of perfume can become insoluble in the surfactant composition, leading to instability. At some point, the amount of perfume exceeds the capacity of the micelles and the composition becomes unstable and no longer transparent, which is a consumer desirable quality, and the viscosity is reduced. To combat low viscosity and lack of transparency, more surfactant can be added. This approach often results in a composition that is costly to make. In addition, increasing perfume levels in a composition can be harmful to cleaning and stability of the cleansing foam, due to the hydrophobic nature of the perfume oil causing it to behave like a "soil" towards the detergency aspects of the surfactant. Micelle compositions with acceptable viscosity often require as much as 15 wt. % or even 18 wt. % surfactant when 2 wt. % or more perfume is used.

Various means to overcome this problem have been suggested. Perfume microcapsules have been developed to encapsulate perfume and protect it from contact with surfactant. However, only a limited number of perfume molecules are stable in perfume microcapsules; and the perfume microcapsule itself must then be delivered to the skin and, later, mechanically crushed by the consumer in order to release the perfume. Most perfume microcapsules are themselves washed down the drain during cleansing, affording little benefit.

Additionally, personal cleansing compositions have been formulated as micelles. Surfactants have a critical micelle concentration, or CMC, at which they aggregate. Below the CMC surfactant exists as monomers in solution. It has been suggested that dilution to below the CMC can release perfume to increase bloom. The problem with this approach is the CMC is very low, often about 100 ppm for cleansing surfactant mixtures (i.e., 0.01 wt. %, a dilution of more than 500-fold from an original composition). Thus, the CMC occurs at concentrations not relevant to cleansing nor rinsing the body. During rinsing, the CMC is reached only at the very end of cleansing, by which time nearly all the cleansing components have already been washed down the drain in the form of micelles, carrying the perfume with them. Relevant dilutions during cleansing are less than 10-fold, especially less than 5-fold, during which time there is extensive exposure of the wash composition to the body and to the air in the shower, affording both time and opportunity for perfume to bloom and partition to the skin, if it can be removed from the environment of the micelle.

The personal cleansing compositions can also deliver similar or enhanced initial perfume perception, similar or enhanced perfume bloom during cleansing and similar or perfume retention on the skin after cleansing.

Surprisingly, inventors have discovered that the specific C13 alkyl sulfate anionic surfactant as described herein can deliver similar or enhanced initial perfume perception, similar or enhanced perfume bloom during cleansing and similar or enhanced perfume retention on the skin after cleansing.

Without wishing to be limited by theory, the personal cleansing composition comprising the specific C13 alkyl sulfate anionic surfactant as described herein can provide the perfume related benefits. Also, the perfume related benefits were believed to result, at least in part, when at least a portion of the perfume in a composition exists in the physical form of a perfume microemulsion within the lamellar phase. This is due to the personal cleansing composition as being proximal to a microemulsion, that is able to lead to a perfume microemulsion. In the microemulsion form, it is believed most perfume is in a central core region and not close in terms of molecular distance to the surfactant hydrocarbon, therefore it is not in a solvent-solute relationship which can reduce perfume activity coefficient.

The result is bloom and/or relative bloom is similar or significantly enhanced, sometimes doubled or even tripled or more; and scent of perfume over the skin after wash, can be similar or enhanced by a similar magnitude.

The personal cleansing composition may already contain a microemulsion phase. The microemulsion phase may be in equilibrium with the lamellar phase.

Personal cleansing compositions are in a lamellar phase and may co-exist with a microemulsion phase or so proximal to a microemulsion phase prior to dilution during use, but can be transformed completely to a perfume microemulsion during use. In fact, there is no need to transform the composition to a perfume microemulsion upon dilution because a microemulsion may already or almost co-exist to provide perfume related benefits.

Optionally, further dilutions of the personal cleansing compositions may lead to an increased microemulsion phase from the lamellar phase.

To make a personal cleansing composition as proximal to a microemulsion form or a perfume microemulsion upon dilution, sufficiency of perfume, which is the oil component for making a perfume core; the specific C13 alkyl sulfate anionic surfactant as described herein, the right level of the surfactant; and hydric solvents are believed to be contributing factors. Hydric solvents have multiple effects like, reducing the dielectric of the water phase, acting as a solvent for the surfactant head groups, reducing interfacial tension between the aqueous phase and hydrocarbon, and interacting with the perfume in the core. During use of the personal cleansing composition, as the composition is diluted, hydric solvents are reduced in concentration, the composition begins to transition into a perfume microemulsion because of the abundance of water added during washing and rinsing. This provides a further benefit to increase perfume activity coefficient by increasing perfume molar concentration in the core. Thus, a sufficient amount of hydric solvents in the initial composition will form a microemulsion phase proximal to a lamellar phase, without the need of a further dilution, which can increase perfume activity during use.

Perfume is a benefit agent. Perfume benefits can be realized at different time points for cleansing compositions. Perfume in the package headspace can be important to select a product at the time of purchase. Perfume scent during cleansing, upon introduction of modest amounts of water, such as for example about 3 parts of water per part composition (i.e., a 3:1 dilution ratio), provides a benefit during skin cleansing. During skin cleansing, some perfume can partition into the outer layers of the skin, which can provide a scented skin benefit for a period of time after cleansing, called scent longevity. A governing property for both scent bloom and longevity is the activity coefficient of the perfume molecules, which is a thermodynamic term. Perfume molecules exhibit their maximum vapor pressure only when they are pure. Diluted perfume molecules, whether diluted by surfactant in a micelle, organic solvent, water, etc., exhibit less than their pure vapor pressure. The amount of perfume in a headspace over a composition, diluted composition, or over the skin can be measured analytically, as described in the methods section below. Benefits in initial fragrance intensity, bloom, or longevity can be demonstrated by comparing performance of the compositions before, during, and, or after a skin cleansing event, compared to conventional body wash or shampoo compositions.

Additionally, perfume analysis in the headspace is directly relatable to the perfume solvent environment in a composition or a diluted composition, so that gas chromatography—mass spectrometry (GCMS) headspace measures are an indicator of the perfume environment, i.e., the microemulsion phase and the perfume relationship to solvent molecules therein. Well established physical laws govern the relationship between concentration of molecules in the headspace, and the solvent environment of the molecules in solution, e.g., Raoult's Law. Likewise, headspace measurements over the skin after washing are similarly useful, since perfume partitioning into the skin is enhanced by perfume activity coefficient, as previously discussed.

In addition to being a benefit agent, perfume is an oil and therefore can be a direct contributor to formation of phases responsible for its activity coefficient (as noted above), and therefore to scent bloom and longevity benefits. As discussed above, perfume oil can generally be added into micelle surfactant mixtures only to about 0.25 weight fraction of the surfactant before it phase separates, whereas diluted cleansing compositions described herein can hold at least 0.5 parts perfume:surfactant, or even 0.75 parts perfume:surfactant, or even more, while remaining transparent, including water diluted compositions.

Perfume can be a carrier for non-scented, hydrophobic additives. Additives which are at least 5 wt. %, or at least 10 wt. %, or at least 20 wt. % miscible with perfume may be employed to increase delivery of the additives to the skin. Any additive which provides a benefit to the skin or the skin environment (e.g., the skin microbiome) may be employed. The additive may provide a direct or indirect benefit, such as antibacterial, antihyperproliferative, anti-inflammatory, chelation, pH regulation, antifungal, antiviral, control of disorders such as acne, atopic dermatitis, eczema, dermatitis, dandruff, antiaging, antiwrinkle, age spot reduction, sunscreen, hydration, moisturization, or any other skin benefit. An advantage of the personal cleansing compositions is enhanced additive delivery to the skin during cleansing. A further benefit is reduction in activity coefficient of the additive by dilution with perfume is transient due to subsequent evaporation of the perfume on the skin, which increases the thermodynamic activity of the additive after its delivery to the skin. Perfume may also provide benefits beyond scent, for example some have antimicrobial activity when delivered to the skin.

Optionally, at least a portion of the personal cleansing composition may be diluted with water at a weight ratio water:composition from about 2:1 to about 10:1, preferably from about 3:1 to about 10:1, more preferably from about 5:1 to about 8:1. The personal cleansing composition may be a rinse-off composition.

Certain microemulsions may be in equilibrium with other phases during dilution of the composition during use. There may be advantages for both the microemulsion and micelle phases to coexist, since micelles may provide superior lather and cleaning properties at the same time the microemulsion may deliver enhanced perfume benefits. Certain analytical measures, such as neutron scattering, dynamic light scattering and optical light transmission, can be used as guides, when evaluating microemulsion phases.

In accordance with the above, a personal cleansing composition comprises a surfactant including a C13 alkyl sulfate anionic surfactant and a cosurfactant, a hydric solvent, perfume, and water. Additionally, optional ingredients may also be included as noted herein, for example, preservatives, thickeners, hydrophobic oils, pH modifiers, additives, soap, etc. The personal cleansing composition may not be in the form of a ringing gel. The personal cleansing composition has at least a portion in a lamellar phase. The personal cleansing composition may be in the form of a microemulsion or may contain a microemulsion phase.

For this, inventors have found that the personal cleansing compositions require a surfactant, a perfume and a hydric solvent in determined proportions to be delivered in a personal cleansing composition that is structured. At least a portion of the composition may be in a lamellar phase. The composition may be in the form of a microemulsion or may contain a microemulsion phase.

Personal Cleansing Compositions

A personal cleansing composition is provided and comprises from about 30% to about 50%, preferably from about 32% to about 45%, more preferably from about 35% to about 40% by weight of the composition, of a surfactant. The surfactant comprises a C13 alkyl sulfate anionic surfactant and a cosurfactant.

The C13 alkyl sulfate anionic surfactant consists of:
(a) less than about 40% by weight of the C13 alkyl sulfate anionic surfactant of a linear C13 alkyl sulfate, and
(b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight by weight of the 2-branched C13 alkyl sulfate anionic surfactant of the 2-branched of 2-methyl dodecyl sulfate anionic surfactant; and
(c) less than about 5% by weight of the C13 alkyl sulfate anionic surfactant of other branched C13 alkyl sulfate anionic surfactant,
wherein (a), (b) and (c) add up to about 100% by weight of the C13 alkyl sulfate anionic surfactant.

The personal cleansing composition also comprises:
from about 4.5% to about 25%, preferably from about 7% to about 22%, more preferably from about 8% to about 20% by weight of the composition, of a perfume;
from about 3% to about 15%, preferably from about 4% to about 13%, more preferably from about 5% to about 11% by weight of the composition, of a hydric solvent; and water.

The personal cleansing composition is structured, preferably at least a portion of the composition is in a lamellar phase.

The lamellar phase of the personal cleansing composition can be characterized by its rheological property (G'), elasticity, and microscopic birefringence.

The personal cleansing composition may contain a microemulsion phase.

The personal cleansing composition may contain a microemulsion phase, wherein the microemulsion phase is in equilibrium with a lamellar phase.

Alternatively, a personal cleansing composition is provided and comprises a surfactant. The surfactant comprises a C13 alkyl sulfate anionic surfactant and a cosurfactant.

The C13 alkyl sulfate anionic surfactant consists of:
(a) less than about 40% by weight of the C13 alkyl sulfate anionic surfactant of a linear C13 alkyl sulfate, and
(b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight by weight of the 2-branched C13 alkyl sulfate anionic surfactant of the 2-branched of 2-methyl dodecyl sulfate anionic surfactant; and
(c) less than about 5% by weight of the C13 alkyl sulfate anionic surfactant of other branched C13 alkyl sulfate anionic surfactant,
wherein (a), (b) and (c) add up to about 100% by weight of the C13 alkyl sulfate anionic surfactant.

In this alternative, the personal cleansing composition also comprises a perfume at a weight ratio perfume:surfactant of at least about 1:10, a hydric solvent at a weight ratio hydric solvent:surfactant of at least about 2:9; between about 25% to about 50% water by weight of the composition, wherein the personal cleansing composition has an elastic modulus G' at 1 Hz from about 70 Pa to about 2500 Pa according to the G' and G" Test Method as disclosed herein.

In this alternative, the personal cleansing composition may comprise a perfume at a ratio of from about 1:10 to 7:10, preferably from about 2:10 to 6:10, more preferably from about 3:10 to 5:10 to the surfactant, a hydric solvent at a ratio from about 2:9 to 2:5, preferably from about 2:8 to 2:5, more preferably from about 2:7 to 2:5 to the surfactant, between about 25% to about 50% water by weight of the composition, wherein the personal cleansing composition has an elastic modulus G' at 1 Hz from about 75 Pa to about 1000 Pa, preferably from about 100 Pa to about 850 Pa, more preferably from about 150 Pa to about 775 Pa according to the Test Method as disclosed herein.

Surfactant

A personal cleansing composition includes a surfactant. Surfactants can help to provide a cleaning benefit, lather properties, and rheology properties to the compositions. The surfactant comprises a C13 alkyl sulfate anionic surfactant and a cosurfactant.

The personal cleansing composition comprises from about 30% to about 50%, preferably from about 32% to about 45%, more preferably from about 35% to about 40%, most preferably from about 36% to about 39% by weight of the composition, of a surfactant, wherein the surfactant comprises a C13 alkyl sulfate anionic surfactant and a cosurfactant.

The total weight percentages of surfactant mentioned previously in the composition include the C13 alkyl sulfate anionic surfactant and any cosurfactant.

The personal cleansing composition may include a C13 alkyl sulfate anionic surfactant at a level of from about 19% to about 43%, from about 22% to about 40%, or from about 24% to about 38%, by weight of the composition.

C13 Alkyl Sulfate Anionic Surfactant

The C13 alkyl sulfate anionic surfactant as described herein can be used for personal cleansing compositions selected from the group consisting of personal bar soap, hand soap, shower gels, a shower or bath cream, a foaming body wash, and mixtures thereof.

The C13 alkyl sulfate anionic surfactant consists of: a) less than about 40% by weight of the C13 alkyl sulfate anionic surfactant of a linear C13 alkyl sulfate, b) more than about 60% by weight of the C13 alkyl sulfate anionic surfactant of a 2-branched C13 alkyl sulfate anionic surfactant; and c) less than about 5% by weight of the C13 alkyl sulfate anionic surfactant of other branched C13 alkyl sulfate anionic surfactant, wherein (a), (b) and (c) add up to 100% by weight of the C13 alkyl sulfate anionic surfactant.

The 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant.

Alternatively, the 2-branched C13 alkyl sulfate anionic surfactant comprises 2-branched alkyl chains: about 25% or less by weight of the 2-branched alkyl chains of 2-pentyl octyl, and more than about 25% by weight of the 2-branched alkyl chains of 2-methyl dodecyl.

By C13 alkyl sulfate anionic surfactant, it is meant that the alkyl sulfate anionic surfactant comprises an alkyl chain which consists of 13 carbon atoms. Thus, for blends of alkyl sulfate anionic surfactant having an average chain length of 13 carbon atoms, only those alkyl sulfate anionic surfactants which comprise a C13 alkyl chain fall under the definition of C13 alkyl sulfate anionic surfactant.

For blends of alkyl sulfate anionic surfactant comprising a mixture of different chain lengths including a C13 alkyl subfraction, independent of the average alkyl chain length, solely this C13 alkyl subfraction falls under the definition of C13 alkyl sulfate anionic surfactant.

With regards to the specific degree and type of C2-branching, the C13 alkyl sulfate anionic surfactant may consist of: a) less than about 30%, preferably from about 5.0% to about 25% by weight of the C13 alkyl sulfate anionic surfactant of the linear C13 alkyl sulfate; b) more than about 70%, preferably from about 75% to about 95% by weight of the C13 alkyl sulfate anionic surfactant of the 2-branched C13 alkyl sulfate anionic surfactant; and c) less than about 3.0%, preferably from about 0.1% to about 2.0% by weight of the C13 alkyl sulfate anionic surfactant of other branched C13 alkyl sulfate anionic surfactant.

The 2-branched C13 alkyl sulfate anionic surfactant may comprise: less than about 20%, preferably from about 5.0% to about 20%, more preferably from about 10% to about 20%, by weight of the 2-branched alkyl chains of 2-pentyl octyl, and more than about 30%, preferably from about 30% to about 50%, more preferably from about 33% to about 50%, by weight of the 2-branched alkyl chains of 2-methyl dodecyl.

Alternatively, the 2-branched C13 alkyl sulfate anionic surfactant may comprise less than about 20%, preferably from about 5.0% to about 20%, more preferably from about 10% to about 20%, by weight of the 2-branched C13 alkyl sulfate anionic surfactant of 2-pentyl-1-octyl sulfate anionic surfactant, and more than about 30%, preferably from about 30% to about 50%, more preferably from about 33% to about 50%, by weight of the 2-branched C13 alkyl sulfate anionic surfactant of 2-methyl-1-dodecyl sulfate anionic surfactant.

Alternatively, the 2-branched C13 alkyl sulfate anionic surfactant may comprise less than about 20%, preferably from about 5.0% to about 20%, more preferably from about 10% to about 20%, by weight of the C13 alkyl sulfate anionic surfactant of 2-pentyl-1-octyl sulfate anionic surfactant, and more than about 28%, preferably from about 28% to about 50%, more preferably from about 29% to about 50%, by weight of the C13 alkyl sulfate anionic surfactant of 2-methyl-1-dodecyl sulfate anionic surfactant.

The remaining fraction within the 2-branched C13 alkyl sulfate anionic surfactant can comprise 2-ethyl-1-undecyl sulfate anionic surfactant (preferably at a level about 25% or less, more preferably about 20% or less, most preferably from about 10% to about 20%, by weight of the 2-branched C13 alkyl sulfate anionic surfactant), 2-propyl-1-decyl sulfate anionic surfactant (preferably at a level about 25% or less, more preferably about 20% or less, most preferably from about 10% to about 18% by weight of the 2-branched C13 alkyl sulfate anionic surfactant) and 2-butyl-1-nonyl sulfate anionic surfactant (preferably at a level about 25% or less, more preferably about 20% or less, most preferably from about 5% to about 18%, by weight of the 2-branched C13 alkyl sulfate anionic surfactant).

Alternatively, the remaining fraction within the 2-branched C13 alkyl sulfate can comprise 2-ethyl-1-undecyl sulfate anionic surfactant (preferably at a level about 25% or less, more preferably about 20% or less, most preferably from about 10% to about 18% by weight of the C13 alkyl sulfate anionic surfactant), 2-propyl-1-decyl sulfate anionic surfactant (preferably at a level about 25% or less, more preferably about 20% or less, most preferably from about 10% to about 15% by weight of the C13 alkyl sulfate anionic surfactant) and 2-butyl-1-nonyl sulfate anionic surfactant (preferably at a level about 25% or less, more preferably about 20% or less, most preferably from about 5% to about 15% by weight of the C13 alkyl sulfate anionic surfactant).

Hence, the distribution of the 2-branched C13 alkyl sulfate with 2-methyl-1-dodecyl sulfate, 2-pentyl-1-octyl sulfate, 2-ethyl-1-undecyl sulfate, 2-propyl-1-decyl sulfate and 2-butyl-1-nonyl sulfate can be provided either by weight of the 2-branched C13 alkyl sulfate anionic surfactant, or by weight of the C13 alkyl sulfate anionic surfactant.

As such, the alkyl chains of the C13 alkyl sulfate anionic surfactant are highly branched, having an increased methyl to pentyl branching ratio compared to other highly branched alcohols such as for example those sold under the Isalchem® trademark which have a much higher pentyl to methyl branching ratio. The average degree of branching is much higher than lower branched alkyl alcohols produced via the OXO process, such as those sold under the Neodol® trademark. Such Neodol® alkyl alcohols have a weight average degree of branching of around 18%.

The personal cleansing composition may be substantially free, or free of alkoxylated anionic sulfate surfactant. Preferably, the personal cleansing composition may be substantially free, or free of ethoxylated anionic sulfate surfactant.

The C13 alkyl sulfate anionic surfactant may be substantially free, or free of alkoxylated anionic sulfate surfactant. In other words, the C13 alkyl sulfate anionic surfactant may have an average degree of alkoxylation of less than 0.5, of less than 0.25, preferably less than 0.1, more preferably is free of alkoxylation.

Preferably, the C13 alkyl sulfate anionic surfactant may be substantially free, or free of ethoxylated anionic sulfate surfactant. In other words, the C13 alkyl sulfate anionic surfactant may have an average degree of ethoxylation of less than 0.5, of less than 0.25, preferably less than 0.1, more preferably is free of ethoxylation.

The average degree of alkoxylation is the mol average degree of alkoxylation (i.e., mol average alkoxylation degree) of all the C13 alkyl sulfate anionic surfactant. Hence, when calculating the mol average alkoxylation degree, the moles of C13 non-alkoxylated sulfate anionic surfactant are included:

*Mol* average alkoxylation degree=($x1$*alkoxylation degree of surfactant 1+$x2$*alkoxylation degree of surfactant 2+ . . . )/($x1+x2+$ . . . )

wherein $x1, x2, \ldots$ are the number of moles of each alkyl (or alkoxy) sulfate anionic surfactant of the mixture and alkoxylation degree is the number of alkoxy groups in each alkyl sulfate anionic surfactant.

Suitable alkyl sulfate anionic surfactants can be made using the following process.

A two-step process can be used to produce branched aldehyde products from linear alpha olefin feedstocks, from which the C13 alkyl sulfate anionic surfactants as described herein can be derived. The two-step process uses a rhodium organophosphorus catalyst for both a first process step and a second step. The first step is an isomerization reaction step and the second process step is a hydroformylation reaction step. The branched aldehydes can undergo a further hydrogenation step to produce branched alcohols.

The isomerization and hydroformylation reactions disclosed herein can be catalyzed by a rhodium organophosphorus catalyst which can be at least one of: (1) an organometallic complex of rhodium and one type of an organophosphorus ligand; (2) or an organometallic complex of rhodium and more than one type of an organophosphorus ligand.

The organophosphorous ligand can be a phosphine. In a nonlimiting example of a phosphine ligand, the phosphine ligand can be triphenylphosphine. The organophosphorous ligand can also be a phosphite. In a nonlimiting example of a phosphite ligand, the phosphite ligand can be tris (2, 4-di-t-butylphenyl) phosphite. A mixture of organophosphorous ligands of different types can also be used, such as a mixture of a phosphine and a phosphite. In a nonlimiting example of a mixture of organophosphorous ligands, the organophosphorous ligands can be a mixture of triphenylphosphine and tris (2, 4-di-t-butylphenyl) phosphite. The reaction system can contain an inert high-boiling solvent, for example a polyalphaolefin. The first catalyst can be formed when the molar ratio of phosphorous to rhodium is in a range of 1:1 to 1000:1, or 5:1 to 50:1, or 15:1 to 25:1. The rhodium concentration can be in a range of 1 ppm to 1000 ppm, or 10 ppm to 200 ppm, or 25 ppm to 75 ppm. The Carbon Monoxide (CO) to Hydrogen ($H_2$) molar ratio can be in a range of 10:1 to 1:10, or 2:1 to 1:2, or 1.3:1 to 1:1.3.

During the isomerization reaction, the first step can be a reaction isomerizing a linear alpha olefin in the presence of Carbon Monoxide (CO) and Hydrogen ($H_2$) at a first pressure. The isomerizing can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. The isomerization reactions can produce an isomerized olefin comprising linear internal olefins of the same or different types.

The isomerization step can be performed at a temperature in a range of 30° C. to 500° C., or 50° C. to 150° C., or 70° C. to 100° C. The isomerization step can be performed at a gauge pressure in a range of 0.1 bar (0.01 MPa above atmospheric) to 10 bar (1 MPa above atmospheric), or 0.5 bar (0.05 MPa above atmospheric) to 5 bar (0.5 MPa above atmospheric), or 1 bar (0.1 MPa above atmospheric) to 2 bar (0.2 MPa above atmospheric).

The isomerizing step can produce a reaction product comprising a 20 wt. % or greater isomerized olefin, or a 40 wt. % or greater isomerized olefin, or a 60 wt. % or greater isomerized olefin, or a 90 wt. % or greater isomerized olefin.

During the hydroformylation reaction step, the isomerized olefin is hydroformylated in the presence of CO and $H_2$ at a second pressure higher than the first pressure to produce a branched aldehyde. The hydroformylation reaction can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. The resultant branched aldehyde is a 2-alkyl branched aldehyde. The linear alpha olefin is 1-dodecene and the branched aldehyde is a branched C13 aldehyde.

The hydroformylating step can be performed at a temperature in a range of 30° C. to 500° C., or 50° C. to 150° C., or 70° C. to 100° C. The hydroformylating step can be performed at a gauge pressure in a range of 5 bar (0.5 MPa above atmospheric) to 400 bar (40 MPa above atmospheric), or 10 bar (1.0 MPa above atmospheric) to 100 bar (10 MPa above atmospheric), or 15 bar (1.5 MPa above atmospheric) to 20 bar (2 MPa above atmospheric).

The hydroformylating step can produce a reaction product comprising a 25 wt. % or greater branched aldehyde, or a 40 wt. % or greater branched aldehyde, or a 60 wt. % or greater branched aldehyde, or a 90 wt. % or greater branched aldehyde.

The products of the hydroformylation reaction can be distilled. The process can have the step of separating the branched aldehyde products resulting from hydroformylation as an overhead product from the first catalyst stream via a distillation process. The distillation step can be performed at a temperature in a range of 100° C. to 200° C., or 125° C. to 175° C. The distillation step can be performed under vacuum at a pressure of less than 500 millibar absolute (0.05 MPa), or less than 100 millibar absolute (0.01 MPa), or less than 30 millibar absolute (0.003 MPa), The process can also have the steps of: hydrogenating the branched aldehyde product in the presence of a hydrogenation catalyst to produce a branched alcohols product composition. The hydrogenating catalyst can be a base metal catalyst, a supported nickel catalyst, a supported cobalt catalyst, a Raney® (W. R. Grace & Co., 7500 Grace Drive, Columbia, MD 21044) nickel catalyst or a precious metal catalyst. The hydrogenating step can be performed at a temperature in a range of 30° C. to 500° C., or 50° C. to 200° C., or 100° C. to 150° C. The hydrogenating step can be performed at a gauge pressure in a range of 5 bar (0.5 MPa above atmospheric) to 400 bar (40 MPa above atmospheric), or 10 bar (1 MPa above atmospheric) to 100 bar (10 MPa above atmospheric), or 30 bar (3 MPa above atmospheric) to 50 bar (5 MPa above atmospheric).

The hydrogenating step can produce a reaction product comprising 25 wt. % or greater branched alcohols, or 40 wt. % or greater branched alcohols, or 60 wt. % or greater branched alcohols, or 90 wt. % or greater branched alcohols.

The C12 olefin source used in the hydroformylation to make the starting C13 aldehydes and subsequent alcohols of use in the present invention can have low levels of impurities that lead to impurities in the starting C13 alcohol and therefore also in the C13 alkyl sulfate. While not intending to be limited by theory, such impurities present in the C12 olefin feed can include vinylidene olefins, branched olefins, paraffins, aromatic components, and low levels of olefins having chain-lengths other than 12 carbons. Branched and vinylidene olefins are typically at or below 5% in C12 alpha olefin sources. Impurities in the resulting C13 alcohols can include low levels of linear and branched alcohols in the range of C10 to C16 alcohols, especially C11 and C15 alcohols, typically less than 2% by weight of the mixture, preferably less than 1%; low levels of branching in positions other than the 2-alkyl position resulting from branched and vinylidene olefins are typically less than about 5% by weight of the alcohol mixture, preferably less than 2%; paraffins and olefins, typically less than 1% by weight of the alcohol mixture, preferably less than about 0.5%; low levels of aldehydes with a carbonyl value typically below 500 mg/kg, preferably less than about 200 mg/kg. These impurities in the alcohol can result in low levels of paraffin, linear and branched alkyl sulfates having total carbon numbers other than C13, and alkyl sulfates with branching in positions other than the 2-alkyl location, wherein these branches can vary in length, but are typically linear alkyl chains having from 1 to 6 carbons. The step of hydroformylation can also yield impurities, such as linear and branched paraffins, residual olefin from incomplete hydroformylation, as well as esters, formates, and heavy-ends (dimers, trimers). Impurities that are not reduced to alcohol in the hydrogenation step may be removed during the final purification of the alcohol by distillation.

Alkyl sulfates are typically prepared by the reaction of fatty alcohols with sulfur trioxide ($SO_3$) or its derivatives or by the reaction of unsaturated compounds with sulfuric acid. Processes using sulfur trioxide in particular have gained prominence for fabricating alkyl sulfate anionic surfactants for use in detergent compositions.

Suitable derivatives of Sulfur trioxide include sulfur trioxide complexes such as chlorosulfonic acid, sulfuric acid, or sulfamic acid. Sulfur trioxide is preferred since it tends to result in more pure products. The sulfation reaction typically takes place in a continuous process using a cascade, falling film or tube bundle reactor, with the sulfur trioxide being applied in an equimolar or small excess, usually in a temperature range of 20° C. to 60° C., with the reaction temperature being determined at least partially by the solidification point of the fatty alcohol in the reaction. The reaction typically results in the acid form of the C13 alkyl sulfate anionic surfactant which is typically neutralized in a subsequent step, using an alkali such as sodium hydroxide, potassium hydroxide, magnesium hydroxide lithium hydroxide, calcium hydroxide, ammonium hydroxide, monoethanolamine, diethanolamine, triethanolamine, monoisopropanolamine, diamines, polyamines, primary amines, secondary amines, tertiary amines, amine containing surfactants, and mixtures thereof.

Also, it is well known that the process of sulfating fatty alcohols to yield alkyl sulfate anionic surfactants also yields various impurities. The exact nature of these impurities depends on the conditions of sulfation and neutralization. Generally, however, the impurities of the sulfation process include one or more inorganic salts, unreacted fatty alcohol, and olefins ("The Effect of Reaction By-Products on the Viscosities of Sodium Lauryl Sulfate Solutions," Journal of the American Oil Chemists' Society, Vol. 55, No. 12, p. 909-913 (1978), C. F. Putnik and S. E. McGuire). The level of non-alkyl sulfate impurities in the alkyl sulfate anionic surfactant of the present invention can be less than 6% by weight, preferably less than 4% by weight, and most preferably less than 2% by weight of the alkyl sulfate anionic surfactant.

For alkyl alkoxy sulfates, the fatty alcohol is first alkoxylated before sulfation. Alkoxylation is a process that reacts lower molecular weight epoxides (oxiranes), such as ethylene oxide, propylene oxide, and butylene oxide with the fatty alcohol. These epoxides are capable of reacting with the fatty alcohol using various base or acid catalysts. In base catalyzed alkoxylation, an alcoholate anion, formed initially by reaction with a catalyst (alkali metal, alkali metal oxide, carbonate, hydroxide, or alkoxide), nucleophilically attacks the epoxide.

Traditional alkaline catalysts for alkoxylation include potassium hydroxide and sodium hydroxide, which give rise to a somewhat broader distribution of alkoxylates. Other catalysts have been developed for alkoxylation that provide a more narrow distribution of alkoxylate oligomers. Suitable examples of narrow range alkoxylation catalysts include many alkaline earth (Mg, Ca, Ba, Sr, etc.) derived catalysts, Lewis acid catalysts, such as Zirconium dodecanoxide sulfate, and certain boron halide catalysts. A specific average degree of alkoxylation may be achieved by selecting the starting quantities of fatty alcohol and ethylene oxide or by blending together varying amounts of alkoxylated surfactants differing from one another in average degree of alkoxylation.

Additional Anionic Surfactant

The personal cleansing composition may comprise an additional anionic surfactant. The additional anionic surfactant may be a non-alkoxylated, preferably a non-ethoxylated anionic surfactant.

The additional anionic surfactant may be selected from the group consisting of ammonium lauryl sulfate, ammonium C10-15 alkyl sulfate, ammonium C11-15 alkyl sulfate, ammonium decyl sulfate, ammonium undecyl sulfate, triethylamine lauryl sulfate, triethanolamine lauryl sulfate, monoethanolamine lauryl sulfate, diethanolamine lauryl sulfate, lauric monoglyceride sodium sulfate, sodium lauryl sulfate, sodium C10-15 alkyl sulfate, sodium C11-15 alkyl sulfate, sodium decyl sulfate, sodium undecyl sulfate, potassium lauryl sulfate, potassium C10-15 alkyl sulfate, potassium C11-15 alkyl sulfate, potassium decyl sulfate, potassium undecyl sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate, sodium dodecyl benzene sulfonate, sodium cocoyl isethionate and combinations thereof.

Preferably, the additional anionic surfactant may be selected from the group consisting of ammonium lauryl sulfate, ammonium undecyl sulfate, triethylamine lauryl sulfate, triethanolamine lauryl sulfate, monoethanolamine lauryl sulfate, diethanolamine lauryl sulfate, sodium lauryl sulfate, sodium undecyl sulfate, potassium lauryl sulfate, potassium undecyl sulfate, sodium lauroyl sarcosinate, sodium cocoyl isethionate and combinations thereof.

Most preferred, the additional anionic surfactant may be selected from the group consisting of ammonium lauryl sulfate, triethylamine lauryl sulfate, triethanolamine lauryl sulfate, monoethanolamine lauryl sulfate, diethanolamine lauryl sulfate, sodium lauryl sulfate, potassium lauryl sulfate and combinations thereof, even most preferred sodium lauryl sulfate.

The personal cleansing composition may comprise from about 0.5% to about 10%, preferably from about 1% to about 8%, more preferably from about 2% to about 6%, most preferably from about 2.5% to about 5.5% by weight of the composition, of an additional anionic surfactant.

Cosurfactant

The personal cleansing composition may include from about 2.5% to about 5%, preferably from about 2.75% to about 4.75%, more preferably from about 3.0% to about 4.5%, by weight of the composition, of a cosurfactant. The cosurfactant may be, for example, a zwitterionic surfactant, an amphoteric surfactant, a nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the personal cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the personal cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl betaine or alkyl amidopropyl betaine, like cocamidopropyl betaine.

Nonionic surfactants suitable for use in the personal cleansing compositions can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

As noted above, the cosurfactant can include a combination of amphoteric, zwitterionic, and nonionic surfactants. One grouping of exemplary cosurfactants includes sodium lauryl amphoacetate, laurylamidopropyl betaine, cocamidopropyl betaine, lauryl betaine, lauryl amine oxide, or a combination thereof.

Preferably, the cosurfactant may comprise a betaine, an alkyl amidopropyl betaine, cocoamidopropyl betaine, or a combination thereof.

The ratio of the weight percent of C13 alkyl sulfate anionic surfactant to the weight percent of the cosurfactant may be from 20:1 to 4:1, preferably from 9:1 to 5:1, more preferably from 8:1 to 6:1.

Perfume

A personal cleansing composition includes a perfume. A personal cleansing composition comprises from about 4.5% to about 25%, preferably from about 7% to about 22%, more preferably from about 8% to about 20%, even more preferably from about 9% to about 15%, by weight of the composition, of perfume.

Perfume may include solvents such as triethyl citrate, isopropyl myristate, dipropylene glycol, or others, to help, for example, with the miscibility of the perfume molecules with each other or to reduce cost. Generally these perfume solvents provide minimal or negligible effects on surfactant compositions as a whole due to the low amount of perfume in the total composition and the amount of solvent in a perfume can be ignored. However, when solvent in the perfume accounts for more than about 5 wt. % of the total hydric solvent in the cleansing composition, it should be accounted for. For example, when a perfume containing 10% hydric solvent is added to a cleansing composition at a level of 10 wt. % and the composition has 10 wt. % of added hydric solvent, the 1 wt. % of hydric solvent from the perfume accounts for a 9% increase in hydric solvent in the cleansing composition (1/11). Since this is more than a 5% change in the hydric solvent in the composition, it can be important. In this case, hydric solvent from the perfume is added (mathematically) to the hydric solvent from other sources added to the composition; and perfume is considered to comprise only the scented molecules and not the solvent, which is subtracted from the wt. % perfume in the composition.

In addition, the weight ratio of perfume to surfactant can impact the ability of the composition to provide an enhanced fragrance benefit. Without being limited by theory, it is believed at least some of the perfume benefits, like bloom and residual scent are derived from an abundance of perfume on the basis of its relation to the surfactant due at least in part to the interaction of the perfume with surfactant as the composition is diluted. Perfume is soluble in surfactant micelles only to about 25% by weight of the surfactant. Above this level, the composition can become unstable unless steps are taken to form a phase to accept the abundance of perfume. However, forming those phases for stability of the perfume circles the composition back to where the perfume is bound within the composition and difficult to release.

As such, a personal cleansing composition comprises from about 2% to about 90%, preferably from about 4% to about 70%, more preferably from about 5% to about 50%, even more preferably from about 8% to about 60%, even much more preferably from about 10% to about 50%, even much more preferably from about 12% to about 40%, or again even much more from about 15% to about 35%, or most preferably from about 20% to about 30%, by weight of the surfactant, of perfume.

The perfume may be at a weight ratio perfume:surfactant of at least about 1:10, preferably from about 1:10 to 7:10, more preferably from 2:10 to 6:10, even more preferably from 3:10 to 5:10.

Perfumes generally contain a broad range of perfume molecules (PRM) having diverse properties. It is an oversimplification to suggest all of the perfume is in a particular location, like in the core of a microemulsion. The real picture is more complex, with perfume molecules in dynamic equilibrium and structures such as micelles and microemulsions can be percolating. Further, some perfume molecules may favor being among surfactant tails or even in the aqueous phase instead of the microemulsion core. In short, all perfume molecules within a perfume mixture do not behave identically. Certain generalizations are useful to explain observed behaviors without inferring that all molecules in a perfume behave identically. For our purposes, a broad array of perfume molecules in a perfume mixture is analyzed by averaging or summing their performance.

Hydric Solvent

A personal cleansing composition includes a hydric solvent. A personal cleansing composition comprises from about 3% to about 15%, preferably from about 4% to about 13%, from about 5% to about 11%, from about 6% to about 11%, or from about 7% to about 11%, by weight of the composition, of the hydric solvent.

The hydric solvent may be selected form the group consisting of glycerin, dipropylene glycol (a glycol ether), diethylene glycol, dibutylene glycol, hexylene glycol, butylene glycol, pentylene glycol, heptylene glycol, propylene glycol, a polyethylene glycol having a weight average molecular weight below about 500, and a combination thereof. One example of a polyethylene glycol is PEG 300. Isomers are included in the generally descriptive solvents listed, for example, butylene glycol is meant to included 1,2-butanediol and 1,3-butanediol and 1,4-butanediol. When solvents are solid in the pure form (e.g., 1,6-hexanediol), they can be melted during the making process and are effective hydric solvents.

The hydric solvent may be preferably a glycol comprising from 3 to 12 carbon atoms, preferably from 3 to 7 carbon atoms, more preferably from 3 to 4 carbon atoms. The hydric solvent may be preferably a glycol selected from the group consisting of hexylene glycol, butylene glycol, pentylene glycol, heptylene glycol, propylene glycol, and mixtures thereof.

Alternatively, the hydric solvent may be preferably a glycol ether comprising from 4 to 12 carbon atoms. The hydric solvent may be preferably a glycol ether selected from the group consisting of dipropylene glycol, diethylene glycol, dibutylene glycol, and mixtures thereof.

Preferably, the hydric solvent may be selected form the group consisting of dipropylene glycol, diethylene glycol, dibutylene glycol, butylene glycol, pentylene glycol, propylene glycol, and a combination thereof.

More preferably, the hydric solvent may be selected form the group consisting of dipropylene glycol, diethylene glycol, dibutylene glycol, pentylene glycol, propylene glycol, and a combination thereof.

Even more preferably, the hydric solvent may be selected form the group consisting of dipropylene glycol (a glycol ether), pentylene glycol, propylene glycol, and a combination thereof.

Most preferably, the hydric solvent may comprise dipropylene glycol.

The personal cleansing composition may preferably comprise from about 3% to about 15%, preferably from about 4% to about 13%, from about 5% to about 11%, from about 6% to about 11%, or from about 7% to about 11%, by weight of the composition, of dipropylene glycol.

In addition, a personal cleansing composition may comprise from about 7% to about 60%, or from about 10% to about 55%, or from about 12% to about 50%, or from about 14% to about 48%, or from about 17% to about 45%, or from about 20% to about 42%, or from about 25% to about 40%, or from about 30%, to 35%, by weight of the surfactant, of hydric solvent. For example, one exemplary cleansing composition will have 6%, by weight of the composition, of hydric solvent, and 44.5%, by weight of the composition, of surfactant. Hydric solvent levels can be expressed as a percent of the surfactant because the solvent molecules can engage with the surfactant molecules.

An intermediate level of hydric solvent can be used to deliver both a combination of exemplary rheology and perfume delivery properties. Thus, the hydric solvent may be from about 15% to about 40%, preferably from about 17% to about 35%, more preferably from about 20% to about 30%, expressed as a weight percent of the surfactant.

The hydric solvent may be at a weight ratio hydric solvent:surfactant of at least about 2:9, preferably from about 2:9 to 2:5, more preferably from 2:8 to 2:5, even more preferably from 2:7 to 2:5.

The hydric solvent may be at a weight ratio hydric solvent:surfactant of at least about 2:9, preferably from about 2:9 to 2:5, more preferably from 2:8 to 2:5, even more preferably from 2:7 to 2:5, wherein the hydric solvent may be selected form the group consisting of dipropylene glycol, diethylene glycol, dibutylene glycol, butylene glycol, pentylene glycol, propylene glycol, and a combination thereof, preferably dipropylene glycol.

Water

A personal cleansing composition includes water. Water may come in with other components or may be added as free water. A personal cleansing composition may comprise from about 5% to about 62.5%, from about 5% to about 50%, from about 6% to about 48%, from about 10% to about 46%, from about 12% to about 45%, or from about 20% to about 40%, by weight of the composition, of water.

Alternatively, the personal cleansing composition may comprise from about 25% to about 50%, from about 28% to about 45%, from about 30% to about 40%, by weight of the composition, of water.

Alternatively, the personal cleansing composition may comprise from about 5% to about 50%, preferably from about 12% to about 45%, more preferably from about 20% to about 40%, by weight of the composition, of water.

In addition, the total weight percent of water and hydric solvent can help to define the amount of solvent phase in which the microemulsion or surfactant structures are distributed. The total amount of solvent phase (approximately, the additive inverse generally of the surfactant level) is a key driver of surfactant phases due to proximity of surfactants.

Thus, the composition may comprise from about 5% to about 75%, from about 15% to about 60%, from about 25% to about 55%, from about 30% to about 53%, by weight of the composition, of the combination of water and hydric solvent.

Rheology—Viscoelasticity and Viscosity

The rheological properties of the personal cleansing compositions can be characterized by viscoelastic parameters and a viscosity. The rheology of a composition can be defined by its G' and G" values, relating to the composition's structure. G' and G" are measured in accordance with the rheological properties method discussed herein. G' and G" describe personal cleansing compositions elastic and viscous response to applied stress, characterizing how the material acts when dispensed from a bottle, sitting on the consumers implement or hand, and how a product spreads on application. It also impacts a consumer's perception of the product, for instance products with low G' values flow too readily in use and are associated in consumer perception and can be perceived as dilute. Conversely products with a high G' are associated in consumer perception with concentrated personal cleansing products. At least a portion of the personal cleansing composition is in a lamellar phase.

Most preferred, the personal cleansing composition may be a stable gel and have a G' at about 1 Hz from about 70 Pa to about 2500 Pa; preferably from about 75 Pa to about 2000 Pa, more preferably from about 80 Pa to about 1500 Pa, even more preferably from about 90 Pa to about 850 Pa, most preferably from 100 Pa to 775 Pa.

In addition, the personal cleansing composition should have a viscosity sufficient to allow it to be dispensed from a package onto an implement or directly onto the skin. At least a portion of the personal cleansing composition is in a lamellar phase.

The viscosity of a personal cleansing composition is measured in accordance with the rheological properties method discussed herein. The personal cleansing composition may have a viscosity at about 0.10 l/sec from about 10 Pa·s to about 1200 Pa·s; from about 20 Pa·s to about 1000 Pa·s, from about 30 Pa·s to about 500 Pa·s, or from about 40 Pa·s to about 300 Pa·s.

Alternatively, the personal cleansing composition may have a viscosity at about 10 l/sec of about 1 Pa·s to about 30 Pa·s; from about 1 Pa·s to about 20 Pa·s, from about 1 Pa·s to about 15 Pa·s, or from about 1 Pa·s to about 10 Pa·s.

Compositions can also be highly shear thinning, having a viscosity ratio of less than about 0.20, or 0.10, or even less than 0.05, which is the ratio of the viscosity at 10 l/sec divided by the viscosity at 0.10 l/sec.

Additives

The personal cleansing composition may comprise an additive. Additives are materials that are at least partially soluble in the perfume. It is believed that additives which are at least partially soluble in the perfume will also exhibit a deposition benefit. Additives which are at least about 5 wt. %, or at least about 10 wt. %, or at least about 20 wt. % miscible with perfume may be employed to increase delivery of the additives to the skin or hair. Some examples of classes of material that can be soluble in the perfume are skin actives, vitamins, antibacterials, antifungals, chelants, or combinations thereof.

Examples of skin actives which can be included are sunscreens; anti-acne medicaments; antioxidants; skin soothing agents, skin healing agents; essential oils, skin sensates, anti-wrinkle medicaments, or mixtures thereof. Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl propionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, magnalol, hinokitiol, honokitiol, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The personal cleansing composition may comprise from about 1% to about 20%, from about 2% to about 10%, or from about 3% to about 8%, by weight of the composition, of an additive.

Hydrophobic Oils

The personal cleansing composition may comprise a hydrophobic oil. Hydrophobic oil can help form a microemulsion phase due to low solubility in the palisade layer of micelles, to further enhance bloom and deposition on skin. The personal cleansing composition may comprise from about 0% to about 25%, from about 2% to about 20%, or from about 3% to about 15% by weight of the composition, of a hydrophobic oil. Exemplary hydrophobic oils can include, for example, isopropyl myristate, isostearyl isostearate, behenyl behenate, triglycerides such as soybean oil, hydrocarbon such as mineral oil, or combinations thereof.

Preservatives

Liquid cleansing compositions often have a high water activity (i.e. about 0.95 or more). Water activity describes the availability of water within a composition to support various chemical and biological processes requiring water. Compositions with high water activity can allow growth of microorganisms and therefore generally utilize preservatives. For example, bacteria can grow at a water activity of about 0.90 or above and fungus can grow at a water activity of about 0.70 or above. Below these water activities, microorganisms generally dehydrate and die.

The personal cleansing compositions may have a relatively low water activity, less than about 0.90. The relatively low water activity allows the compositions to naturally resist the growth of microorganisms and thus utilize minimal or even no, preservative. In addition, the use of high levels (5 wt. % or more) of glycols, like dipropylene glycol, can also help to prevent the growth of microorganisms and further support a composition which needs minimal or even no, preservative.

Thickeners

The personal cleansing compositions may comprise from about 0.1% to about 4% by weight of the composition of a thickener. Preferred thickeners are hydrophilic such as cellulose derivatives, hydrophobically modified celluloses, starches and starch derivatives, polyacrylates including hydrophobically modified polyacrylates and polyacrylamides, bacterial polymers such as xanthan gum, tree and plant gums such as guar, insoluble thickeners such as cellulose.

Soap

The personal cleansing compositions as described herein may also comprise a soap.

Packaging

Personal cleansing compositions can be dispensed from a squeezable package with an orifice, such as a conventional body wash or shampoo package. The package can be a compact package, i.e., contain less than about 250 ml, or 200 ml, or 150 ml of volume to signal the contents are concentrated. The shear thinning compositions can be dispensed from a package with a slit valve orifice or other flexible orifice, which is generally cut from a silicone elastomeric material and inserted into an orifice housing.

When the composition has a relatively low viscosity, preferably less than about 0.25 Pa·s, at 10 l/sec, it can be dispensed from a foaming package such as a pump foamer. Compositions can also be dispensed from liquid pump packages.

Methods

In addition to the compositional elements and parameters noted above, it is believed there are also some inventive benefits and/or uses to the compositions which are set out as methods below. For the sake of brevity, all of the compositional elements and parameters noted above are not repeated herein, but can be used within the methods where relevant.

A method for providing a stable or improved stable gel of a personal cleansing composition comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; water, and wherein at least a portion of the composition is in a lamellar phase. The personal cleansing composition may have an elastic modulus G' at 1 Hz from about 70 Pa to about 2500 Pa according to the G' and G" Test Method as disclosed herein.

Alternatively, a method for providing a stable or improved stable gel of a personal cleansing composition comprising i) a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) a perfume at a weight ratio perfume:surfactant of at least about 1:10; iii) a hydric solvent at a weight ratio hydric solvent:surfactant of at least about 2:9, between about 25% to about 50% water by weight of the composition; wherein the personal cleansing composition has an elastic modulus G' at 1 Hz from about 70 Pa to about 2500 Pa according to the G' and G" Test Method as disclosed herein.

A method for providing a similar or denser lather of a personal cleansing composition, comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; water, and wherein at least a portion of the composition is in a lamellar phase.

A method of providing similar or enhanced fragrance of a personal cleansing composition comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

The rinse-off microemulsion cleansing composition may have a G' at 1 Hz of about 70 Pa to about 2500 Pa. The composition may have a total GCMS count higher than that of a control where the hydric solvent is replaced with water, when the total GCMS count is measured in accordance with the PHADD method at zero dilution. The composition may have a GCMS total count of about 10% more than the control, 15%, 20%, 25%, 50%, 75%, 100%, 150%, 200%, 250%, or even 300% more than the control.

A method of providing similar or enhanced in-vitro bloom of a personal cleansing composition comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

The rinse-off microemulsion cleansing composition may have a G' at 1 Hz of about 70 Pa to about 2500 Pa. The composition may have a total GCMS peak area at the 3:1 dilution point which is at least 1.5 times greater than the GCMS peak area of the composition prior to dilution when measured in accordance with the PHADD method. The composition may have a GCMS peak area of about 1.75 times more than the composition prior to dilution, 2 times, 2.25 times, 2.5 times, 3 times, or even 4 times or more, more than the composition prior to dilution.

A method of providing similar or enhanced fragrance of a personal cleansing composition comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

The rinse-off microemulsion cleansing composition may have a G' at 1 Hz of about 70 Pa to about 2500 Pa. The composition may have a total GCMS count higher than that of a control where the solvent is replaced with water when the total GCMS count is measured in accordance with the PSHAM method. The composition may have a GCMS total count of about 10% more than the control, 15%, 20%, 25%, 50%, 75%, 100%, 150%, 200%, 250%, or even 300% more than the control.

A method of providing similar or enhanced fragrance longevity of a personal cleansing composition comprising i) from about 30% to about 50% by weight of the composition, of a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) from about 4.5% to about 25%, by weight of the composition, of a perfume; iii) from about 3% to about 15%, by weight of the composition, of a hydric solvent; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

The rinse-off microemulsion cleansing composition may have a G' at 1 Hz of about 70 Pa to about 2500 Pa. The composition may have a total GCMS count higher than that of a control where the solvent is replaced with water when the total GCMS count is measured in accordance with the PSHAM method at 1 hour after the initial application. The PSHAM method may also be evaluated at other time points, for example, 2 hours, 3 hours, 3.5 hours, 4 hours, etc. after the initial application. The composition may have a GCMS total count of about 10% more than the control, 15%, 20%, 25%, 50%, 75%, 100%, 150%, 200%, 250%, or even 300% more than the control.

Alternatively, a method of providing similar or enhanced fragrance of a personal cleansing composition comprising i) a surfactant, wherein the surfactant comprises a C13 alkyl sulfate anionic surfactant and a cosurfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; ii) a perfume at a ratio of at least about 1:10 to the surfactant; iii) a hydric solvent at a ratio of at least about 2:9 to the surfactant, between about 25% to about 50% water by weight of the composition; wherein the personal cleansing composition has an elastic modulus G' at 1 Hz from about 70 Pa to about 2500 Pa according to the G' and G" Test Method as disclosed herein.

Uses

In addition to the compositional elements and parameters noted above, it is believed there are also some inventive benefits and/or uses to the compositions which are set out as uses below. For the sake of brevity, all of the compositional elements and parameters noted above are not repeated herein, but can be used within the uses where relevant.

Use of a personal cleansing composition for providing a stable or improved stable gel wherein the personal cleansing composition comprises from about 30% to about 50%, preferably from about 32% to about 45%, more preferably from about 35% to about 40% by weight of the composition, of a surfactant, wherein the surfactant comprises a C13 alkyl sulfate anionic surfactant and a cosurfactant, wherein the C13 alkyl sulfate anionic surfactant consists of: (a) less than about 40% by weight of the C13 alkyl sulfate anionic surfactant of a linear C13 alkyl sulfate, and (b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and (c) less than about 5% by weight of the C13 alkyl sulfate anionic surfactant of other branched C13 alkyl sulfate anionic surfactant, wherein (a), (b) and (c) add up to about 100% by weight of the C13 alkyl sulfate anionic surfactant; from about 4.5% to about 25%, preferably from about 7% to about 22%, more preferably from about 8% to about 20% by weight of the composition, of a perfume; from about 3% to about 15%, preferably from about 4% to about 13%, more preferably from about 5% to about 11% by weight of the composition, of a hydric solvent; and water; wherein the composition is structured, preferably at least a portion of the composition is in a lamellar phase.

Use of a C13 alkyl sulfate anionic surfactant in a personal cleansing composition, as described hereinbefore for providing a stable or improved stable gel. The personal cleansing composition has an elastic modulus G' at 1 Hz from about 70 Pa to about 2500 Pa according to the G' and G" Test Method as disclosed herein.

Use of a C13 alkyl sulfate anionic surfactant in a personal cleansing composition, as described hereinbefore for providing an improved lather stability.

Use of a C13 alkyl sulfate anionic surfactant in a personal cleansing composition, as described hereinbefore for providing a similar or denser lather.

Use of a combination of a C13 alkyl sulfate anionic surfactant in a personal cleansing composition, as described hereinbefore and a cosurfactant, wherein the ratio of the weight percent of C13 alkyl sulfate anionic surfactant to the weight percent of the cosurfactant is from 20:1 to 4:1, preferably from 9:1 to 5:1, more preferably from 8:1 to 6:1 for providing a similar or denser lather. Preferably, the cosurfactant may comprise a betaine, an alkyl amidopropyl betaine, cocoamidopropyl betaine, and a combination thereof.

Use of a C13 alkyl sulfate anionic surfactant in a personal cleansing composition, as described hereinbefore for providing a higher capacity to solubilize fragrance, preferably over sodium trideceth-n sulfate when n is 2 or 3.

Use of a combination between a C13 alkyl sulfate anionic surfactant and a hydric solvent in a personal cleansing composition, as described hereinbefore to provide similar or enhance in-vitro bloom of a personal cleansing composition.

Use of a combination of a C13 alkyl sulfate anionic surfactant and a hydric solvent in a personal cleansing composition, as described hereinbefore to provide similar or enhance fragrance longevity on skin of a personal cleansing composition.

Use of a combination of a C13 alkyl sulfate anionic surfactant and a hydric solvent in a personal cleansing composition, as described hereinbefore to provide similar or enhance fragrance of a personal cleansing composition prior to use.

Use of a combination of a C13 alkyl sulfate anionic surfactant and a hydric solvent in a personal cleansing composition, as described hereinbefore to provide similar or enhance fragrance on skin upon initial application of a personal cleansing composition.

Test Methods

It is understood that the test methods that are disclosed in the Test Methods Section of the present application should be used to determine the respective values of the parameters of Applicants' invention as such invention is described and claimed herein.

Test Methods a) G' and G" Test Method

To measure the viscoelastic properties of a personal care composition, the viscous (G") and elastic (G') moduli, use a rheometer such as a AR G2 Rheometer (TA Instruments, DE, USA) with serrated flat plate upper geometry with a diameter of 40 mm and serrated flat plate lower geometry with Peltier heating/cooling to control temperature. Place approximately 2 gram of personal care composition onto the lower test geometry and lower the upper geometry to 1050 microns gap, lock the geometry and wipe away excess composition to create an even surface around the edge of the geometry, then continue to the 1 mm measurement gap. Conduct the oscillatory test over frequency range of 0.1 to 10 Hz, collecting 5 data points per decade, using a constant oscillatory strain of 0.5% and a temperature of 25° C. The tan delta is calculated as the ratio of G"/G'.

Record the G' and G" (Pa) at a frequency of 1 Hz.

b) Centrifuge Test

Compositions are considered to be structured when they do not separate into two or more visible layers or phases when ultracentrifuged for 10 minutes at 3,000 rpm in a standard benchtop swing-rotor at 25° C.

c) Viscosity Method

To measure the viscosity of a personal care composition use a rheometer such as an AR G2 Rheometer (TA Instruments, DE, USA) set up as set out above. Conduct a continuous flow test at 25° C., controlling the shear rate and progressing from a shear rate of 0.01 to 100 l/sec over a time period of 3 minutes, running the test in log mode and collecting 15 points per decade. Record the viscosity (Pa·s) at the shear rates of interest, for the samples herein we have reported the viscosity at a shear rate of about 0.10 l/sec and about 1 l/sec, interpolating as needed to obtain values at shear rates. Fit the data to a Carreau viscosity model and report the zero shear viscosity (Pa·s).

d) Perfume Headspace Abundance During Dilution Method (PHADD)

1) Perfume Headspace Abundance for Neat Products

Unless otherwise indicated, all laboratory instruments are operated according to manufacturer's instructions. The following equipment is used: 20 mL headspace vials from Gerstel (Baltimore, MD); timer; gas chromatograph (GC) Agilent model 6890 and Gerstel MPS-2 auto sampler; GC column J&W DB5-MS, 30 m×0.25 mm ID, 1.0 μm film thickness obtained from Agilent Technologies, Inc., Wilmington, DE, USA; carrier gas of ultra-pure helium, about 1 mL/min. flow rate; solid-phase microextraction injection port liner (0.75 mm ID) from Supelco; and a model 5973 Mass Selective Detector obtained from Agilent Technologies, Inc., Wilmington, DE, USA having a source temperature of about 230° C., and a MS Quad temperature of about 150° C.

1 gram of cleansing composition is placed into a clean 20 mL headspace vial and a stir bar is added to the vial. A polytetrafluroethylene cap is placed on the vial and hand tightened. The sample is allowed to equilibrate to establish equilibrium of the perfume molecules between the composition and the headspace. This generally takes at least 30 minutes at room temperature. The sample is then analyzed using an automated solid phase microextraction-gas chromatograph-mass spectrometer (SPME-GC-MS) analysis system.

Transfer the sample vials to the auto sampler tray to begin analysis. Start the sequence of sample loading and analysis. Each sample vial is taken by the auto sampler to the incubation chamber and held at 30° C. for 1 minute. The SPME fiber assembly is DVB/CAR/PDMS (50/30 um, 24 ga, 1 cm length). Sampling time is 1 minute. The samples are stirred at 500 rpm during SPME sampling. After sampling, the SPME fiber is injected into the GC injector. The injector temperature is about 270° C.

The GC-MS analysis is started. SPME desorption time is about 5 minutes. The following temperature program is used: i) an initial temperature of about 50° C. which is held for 0.5 minutes, and ii) increase the initial temperature at a rate of about 8° C./min until a temperature of about 275° C. is reached, hold at about 275° C. for 2.5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, DE, USA. To calculate the perfume headspace abundance, all of the area counts of the perfume molecules are added together.

2) Perfume Headspace Abundance for Diluted Product

For the perfume headspace abundance for diluted product, use the method above for neat product, except 1.0 g of product is combined with sufficient water to reach the desired level of dilution, usually between (0.5-5 g), a magnetic stir bar is added to each vial, and after the cap is in place, the vials are stirred via the magnetic bar for at least 30 minutes to equilibrate.

e) Perfumed Skin Headspace Abundance Method (PSHAM)

Unless otherwise indicated, all laboratory instruments are operated according to manufacturer's instructions. The following equipment is used: Stir Bar Sorptive Extraction Sampling Devices—Gerstel Twister, 2 cm in length with 1 mm PDMS (polydimethyl silicone) phase thickness; glass sampling cups with magnets to hold Twisters during sampling—about 35 mL in volume; timer; gas chromatograph (GC) Agilent model 7890 and Gerstel MPS-2 autosampler with thermal desorption unit (TDU) and cooled-on-column (CIS-4) temperature programmable inlet; GC column J&W DB5-MS, 30 m×0.25 mm ID, 1.00 um film thickness obtained from Agilent Technologies, Inc., Wilmington, DE, USA; carrier gas of ultra-pure helium, about 1 mL/min flow rate; liquid nitrogen for injection port cryogenic cooling; Gerstel TDU injection port liners with glass wool; and a detector model 5975 Mass Selective Detector obtained from Agilent Technologies, Inc., Wilmington, DE, USA having a source temperature of about 230° C., and a MS Quad temperature of about 150° C.

Headspace samples are collected from panelists' arms that have been washed with test products and/or controls. The wash protocol includes: 1) adjusting water temperature to about 37.8° C. (100° F.) and water flow to about 1 gallon/min; 2) rinsing the arm under the water stream for about 5 seconds; 3) apply product of known weight on a puff which has been prewetted for 5 seconds with water; 4) lather product in the puff by hands for 10 seconds; 5) wash the entire forearm for 15 seconds using back and forth motion, then wait for about 15 seconds; 6) rinse the arm under the water stream for about 15 seconds; 7) pat dry the forearm using a paper towel; and then 8) proceed to sensory evaluation or analytical sampling. The Twister device is held inside of the sampling cup with magnetic force while the cup is placed against panelists' arms for a period of 3 minutes. The Twister is then transferred to the thermal desorption tube and capped with a transport adapter.

To begin the analysis, transfer the Twister transport tubes to the autosampler tray and proceed with TDU-GC-MS analysis. Set-up the sequence of samples needing to be analyzed and start the sequence of sample loading and analysis. In this step, the Twister transport tube is taken by the autosampler to the thermal desorption unit where it is heated to about 250° C. and held at that temperature for about 5 minutes. Perfume materials that are thermally desorbed from the Twister are trapped by the liquid nitrogen cooled inlet, which is held at about −120° C. during desorption. The programmable temperature inlet is then heated 275° C. and held at that temperature for 3 minutes.

The GC-MS analysis run is started and the GC temperature program is initiated with mass spectrometer detection. The following temperature program is used: i) an initial temperature of about 50° C. which is held for 0.5 minutes, and ii) increase the initial temperature at a rate of about 8° C./min until a temperature of about 275° C. is reached, hold at about 275° C. for 5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, DE, USA. Abundance of perfume in the headspace over the skin is calculated by adding the area counts of all the perfume molecules. The relative enhancement of abundance of perfume in the headspace using test products over control products is obtained by the ratio of the total peak area counts. The PSHAM measurement may be repeated on the target surface at later time intervals to test for longevity of fragrance on the skin. These time intervals could be any desired, for example, 1 hour, 2 hours, 3 hours, 3.5 hours, 4 hours, etc. after the initial application.

f) Cylinder Method

Lather can be measured in accordance with the Cylinder Method. Lather volume is measured using a graduated cylinder and a rotating mechanical apparatus. A 1,000 ml graduated cylinder is used which is marked in 10 ml increments, has a height of 14.5 inches at the 1,000 ml mark from the inside of its base, and has a neck at its top fitted for a plastic insert cap (for example, Pyrex No. 2982). Moderately hard water (about 7 gpg or about 120 ppm) is prepared by dissolving 1.14 grams calcium chloride dihydrate and 1.73 grams magnesium chloride hexahydrate into one U.S. gallon distilled water. The water is maintained at between 40.5-43.3° C. (105-110° F.). The graduated cylinder is heated to about the same temperature by flushing with excess tap water at the same temperature for about 15 seconds, then drying its exterior and shaking briefly upside down to dry the interior. 100.0 grams of the moderately hard water at the indicated temperature is weighed directly into the graduated cylinder. The cylinder is clamped in a mechanical rotating device, which clamps the cylinder vertically with an axis of rotation that transects the center of the graduated cylinder. Using a 3- or 4-place metric balance, invert the plastic cap for the graduated cylinder onto the balance pan and weigh 0.500 grams of composition for compositions less than 19% surfactant (weigh 0.250 grams of composition for compositions greater or equal than 19% surfactant) to within 4 milligrams accuracy, using a holder to keep the cap level. Insert the cap into the graduated cylinder neck while being careful that all composition is now in the space in the cylinder interior. For compositions with very low viscosity which will not remain on the cap surface, 500 mg composition can be added directly to the graduated cylinder. Rotate the cylinder for 25 complete revolutions at a rate of about 10 revolutions per 18 seconds to create a lather and stop in a level, vertical position. When the cylinder stops in a vertical position, start a digital stopwatch. Observing the water draining at the bottom, record the time to the nearest second when the water height measures 50 cc, then 60 cc, then 70 cc and so on until at least 90 cc has drained. Measure and record the total height of the foam in the column interior, which is the lather volume. If the top surface of the lather is uneven, the lowest height at which it is possible to see halfway across the graduated cylinder is the lather volume (ml). If the lather is coarse such that a single or only a few foam cells ("bubbles") reach across the entire cylinder, the height at which at least about 10 foam cells are required to fill the space is the lather volume, also in ml up from the base. When measuring the lather height, bubbles that are larger than about 25.4 mm (1 inch) across at the top surface are considered free air and not lather. The measurement is repeated and at least three results averaged to obtain the lather volume. In a spreadsheet, calculate the lather density at each observed time point as the volume of foam (total height minus water height) divided by the weight of the foam (100.5 grams minus the weight of water observed, using a density of 1.00 g/cc for water). Fit the 3 time points closest to (ideally, also bracketing) 20 seconds to a $2^{nd}$ order polynomial equation. Solve the equation for the lather density at 20 seconds, which is the lather density of the composition. Multiply the lather volume by the lather density to obtain the lather mass, in grams.

The entire measurement process should take less than about 3 minutes in order to maintain desired temperature.

g) Aging Stability Test

A composition is filled into a 118.3 mL (4 fl. oz.) glass jar with minimal headspace and capped, placed in a dark room maintained at 40° C. for 3 months. A composition is stable if there is minimal visual sign of phase separation and the viscosity changes by less than about 90% from the original viscosity.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Examples of Suitable Alkyl Sulfate Anionic Surfactants and Their Synthesis:

The following are representative and non-limiting examples of suitable C13 alkyl sulfate anionic surfactants, including a non-limiting method of synthesis.

Using the above-described processes, the alcohol compositions described below in Alcohol Example 1 are obtained and analyzed by gas chromatography with flame ionization detection (GC/FID). The samples are prepared as a 1% (w/v) dichloromethane solution and injected into a capillary GC Column: DB-1 HT 15 m×0.25 mm ID, 0.1 μm film thickness, using an oven temperature program [initial temperature 80° C. (1 min), ramp 10° C./min to 220° C., ramp 30° C./min to 350° C. (1 min)] for a total run time of 19 minutes. Additional GC parameters include Column Flow: 1.4 ml/min ($H_2$), Injection Temperature: 300° C., Sample Amount: 1 μL, Split Ratio: 1/400, FID Temperature: 350° C., $H_2$ Flow: 40 mL/min, Air Flow: 400 mL/min, and Makeup Gas Flow: 25 mL/min Alcohol Example 1. Synthesis of Narrow Branched Tridecanol (Alcohol 1)

A C12 linear alpha olefin feedstock (1-Dodecene) was obtained from the Chevron Phillips Chemical Company LP, as identified by product name AlphaPlus® 1-Dodecene (Chevron Phillips Chemical Company LP, P.O. Box 4910, The Woodlands, TX 77387-4910, US, phone (800) 231-3260). The homogeneous rhodium organophosphorus catalyst used in this example is prepared in a high pressure, stainless steel stirred autoclave. To the autoclave was added 0.027 wt. % Rh(CO)2ACAC ((Acetylacetonato)dicarbonylrhodium(I)), 1.36 wt. % tris (2,4,-di-t-butylphenyl) phosphite ligand and 98.62 wt. % Synfluid® PAO 4 cSt (Chevron Phillips Chemical Company LP, P.O. Box 4910, The Woodlands, TX 77387-4910) inert solvent. The mixture was heated at 80° C. in the presence of a CO/$H_2$ atmosphere and 2 bar (0.2 MPa above atmospheric) gauge pressure for four hours to produce the active rhodium catalyst solution (109 ppm rhodium, P:Rh molar ratio=20). The 1-Dodecene linear alpha olefin was added to the rhodium catalyst solution in the autoclave producing a starting reaction mixture with a rhodium concentration of 35 ppm. The alpha olefin feed was then isomerized at 80° C. in the presence of a CO/$H_2$ atmosphere and 1 bar (0.1 MPa above atmospheric) gauge pressure for 10 hours. The isomerized olefin was then hydroformylated at 70° C. in the presence of a CO/$H_2$ atmosphere and 20 bar (2 MPa above atmospheric) gauge pressure for 8 hours. The molar ratio of CO to $H_2$ in both the isomerization step and the hydroformylation step was equal to 1:1.15. The resulting hydroformylation reaction product was flash distilled at 140-150° C. and 25 millibar to recover the rhodium catalyst solution as a bottoms product and recover a branched C13 Aldehyde overheads product with a composition comprising:

| | |
|---|---|
| 1-Tridecanal | 13.9 wt % |
| 2-Methyl-dodecanal | 28.3 wt % |
| 2-Ethyl-undecanal | 15.2 wt % |
| 2-Propyl-decanal | 14.5 wt % |
| 2-Butyl-nonanal | 13.6 wt % |
| 2-Pentyl-octanal | 12.6 wt % |
| Other | 1.9 wt % |

The weight % branching in the branched C13 aldehyde product was 86.2%.

The branched C13 aldehyde product was hydrogenated in a high pressure, Inconel 625 stirred autoclave at 150° C. and 20 bar (2 MPa above atmospheric) hydrogen gauge pressure. The hydrogenation catalyst used was a Raney® Nickel 3111 (W. R. Grace & Co., 7500 Grace Drive, Columbia, MD 21044, US, phone 1-410-531-4000) catalyst used at a 0.25 wt. % loading. The aldehyde was hydrogenated for 10 hours and the resultant reaction mixture was filtered to produce a branched C13 alcohol product (Alcohol 1 in Table 1) comprising:

| | |
|---|---|
| 1-Tridecanol | 13.36 wt % |
| 2-Methyl-dodecanol | 28.95 wt % |
| 2-Ethyl-undecanol | 16.25 wt % |
| 2-Propyl-decanol | 13.92 wt % |
| 2-Butyl-nonanol | 13.46 wt % |
| 2-Pentyl-octanol | 13.02 wt % |
| Other | 1.04 wt % |

The weight % 2-alkyl branching in the branched C13 alcohol product was 85.6%.

Alkyl Sulfate Example 1. Synthesis of Narrow Branched Tridecanol Sulfate using a Falling Film Sulfation Reactor The alcohol from Alcohol Example 1 is sulfated in a falling film using a Chemithon single 15 mm×2 m tube reactor using $SO_3$ generated from a sulfur burning gas plant operating at 2.5 kg/h (5.5 lb/hr) sulfur to produce 3.76% $SO_3$ on a volume basis. Alcohol feed rate is 15.2 kg/hour and feed temperature was 27.2° C. (81° F.). Conversion of the alcohol to alcohol sulfate acid mix was achieved with 96.5% completeness. Neutralization with 50% sodium hydroxide is completed at ambient process temperature to 0.65% excess sodium hydroxide. 33 gallons of sodium neutralized C13 narrow branched Alcohol Sulfate paste. Analyses by standard Cationic $SO_3$ titration method determines final average product activity to be 73.4%. The average unsulfated level is 2.10% w/w.

Alkyl Sulfate Example 2. Synthesis of Narrow Branched Tridecanol Sulfate Using a Falling Film Sulfation Reactor with Amine Oxide Addition The alcohol from Alcohol Example 1 is sulfated in a falling film using a Chemithon single 15 mm×2 m tube reactor using $SO_3$ generated from a sulfur burning gas plant operating at 2.3 kg/h (5.0 lb/hr) sulfur to produce 3.76% $SO_3$ on a volume basis. Alcohol feed rate is 13.8 kg/hour and feed temperature was 23.9° C. (75° F.). Conversion of the alcohol to alcohol sulfate acid mix was achieved with 97% completeness. Neutralization is co-neutralized with 50% sodium hydroxide and with C12/14 dimethyl amine oxide at ambient process temperature to a pH of 8.0. 68 kilograms of the C13 narrow branched Alcohol Sulfate/Amine oxide paste was made to a target activity of 51.7% Alcohol sulfate and 11.76% C12/14 dimethyl amine oxide.

The effect of type of branching within the alkyl chain of the C13 alkyl sulfate anionic surfactants was evaluated for performance within personal cleansing formulations in terms of gel stability, structured features, lather stability, miscibility and perfume benefits, following the test methods described hereinabove.

Test Materials:

The relative performance was determined for C13 alkyl sulfate anionic surfactants based on the starting alcohol summarized in Table 1. The starting alcohol ex table 1 consisted essentially of C13 alkyl chains. Alcohol 1 used to make the C13 alkyl sulfate anionic surfactants in the inventive composition has a type of branching as described in the claims and were produced following the making process described herein.

TABLE 1

Alkyl chain distribution of starting C13 alcohols

| | Alcohol 1 from Alcohol Example 1 |
|---|---|
| Alkyl chain length | C13 |
| Linear content[+] | 13.4% |
| 2-Alkyl Branched C13 Alcohol[+] | 85.6% |
| Other [+++] | 1.0% |
| 2-methyl-1-dodecanol[+] | 29.0 |
| 2-ethyl-1-undecanol[+] | 16.2 |
| 2-propyl-1-decanol[+] | 13.9 |
| 2-butyl-1-nonanol[+] | 13.5 |
| 2-pentyl-1-octanol[+] | 13.0 |
| 2-Alkyl Branch distribution: | |
| 2-methyl-1-dodecanol[++] | 33.9% |
| 2-ethyl-1-undecanol[++] | 18.9% |
| 2-propyl-1-decanol[++] | 16.2% |
| 2-butyl-1-nonanol[++] | 15.8% |
| 2-pentyl-1-octanol[++] | 15.2% |

[+]by weight of starting C13 alcohol
[++]by weight of branched C13 alcohol
[+++] such as isomers with branches in non-C2 positions, paraffins, alcohols with chain-lengths other than 13 carbons The starting C13 alcohol of Table 1 was individually sulfated in the pilot plant according to one of the processes as set out above. The resulting alkyl sulfate distribution is retained and corresponds to the distribution of the alkyl chains as set out for the Alcohol 1 in Table 1.

The following compositions were prepared and assessed.

| Compositions (% wt.) | | | | | | |
|---|---|---|---|---|---|---|
| | EXAMPLE | | | | | |
| | A | B | C | D | E | F |
| C13 Alkyl sulfate from Alcohol 1 | 36.8 | 39.6 | 39.6 | 36.7 | 28.3 | 32.6 |
| cocamidopropyl betaine | 5.5 | 5.9 | 5.9 | 5.5 | 4.2 | 4.9 |
| Dipropylene glycol | 13.0 | 13.0 | 6.5 | 6.0 | 9.75 | 7.8 |
| perfume | 9.8 | 6.5 | 13.0 | 12.1 | 22.75 | 17.2 |
| citric acid | | | | qs pH 6 | | |
| water | | | | qs | | |
| total surfactant | 42.3 | 45.5 | 45.5 | 42.2 | 32.5 | 37.5 |
| observations | Translucent stable holding air bubbles | Structured gel | Gel | Translucent rigid gel | Viscoelastic fluid No phase separation | Gel |
| G' at 1 Hz | 584 | 675 | 808 | 2361 | 72 | 767 |
| G'' at 1 Hz | 47.4 | 80 | 83 | 288 | 17 | 68 |
| h zero shear (Pa·s) | 10.9 | 106.7 | 119.4 | 157.4 | 4.14 | 107.5 |
| h 1 s$^{-1}$ shear (Pa·s) | 39.3 | 40.8 | 82.0 | 489.5 | 4.32 | 46.6 |
| Lather volume (mL) | 815 | 855 | 790 | | 630 | |
| Lather density (g/cc) | 0.029 | 0.0319 | 0.0334 | | 0.0373 | |
| Total GCMS headspace counts rel. to control (undiluted) | 2.35 | | | | | |
| Total GCMS headspace counts rel. to control (ave of dilutions 1×-5×) | 2.30 | | | | | |

| | EXAMPLE | | | | | |
|---|---|---|---|---|---|---|
| | G | H | I | J | M | N |
| C13 Alkyl sulfate from Alcohol 1 | 33.9 | 39.6 | 31.1 | 29.7 | 28.9 | 32.1 |
| cocamidopropyl betaine | 5.1 | 5.9 | 4.6 | 4.4 | 4.3 | 4.8 |
| Dipropylene glycol | 8.1 | 14.6 | 13.0 | 9.3 | 13.5 | 5.5 |
| perfume | 17.9 | 4.9 | 16.3 | 21.6 | 18.4 | 22.7 |
| citric acid | | | | qs pH 6 | | |
| water | | | | Qs | | |
| total surfactant | 39.0 | 45.5 | 35.7 | 34.1 | 33.2 | 36.9 |
| observations | Lamellar gel | stable gel | Gel | Gel | Translucent stable gel | separated into <5% top clear >95% bottom structured assume microemulsion is top clear phase |
| G' at 1 Hz (Pa) | 767.3 | 491 | 507.2 | 150 | 85.8 | |
| G'' at 1 Hz (Pa) | 78.2 | 58 | 59.9 | 22.2 | 21.6 | |
| h zero shear (Pa·s) | 67.4 | 93.83 | 425.85 | 11.58 | | |
| h 1 s$^{-1}$ shear (Pa·s) | 45.9 | | | | | |
| Lather volume (mL) | 730 | 1030 | 735 | 740 | 685 | |
| Lather density (g/cc) | 0.0376 | 0.0283 | 0.0339 | 0.0345 | 0.0376 | |

| | COMP. EX. | | | | |
|---|---|---|---|---|---|
| | CEx. A | CEx. B | CEx. C | CEx. D | CEx. E |
| C13 Alkyl sulfate from Alcohol 1 | 17.0 | 28.3 | 17.0 | 39.6 | 28.3 |
| cocamidopropyl betaine | 2.5 | 4.2 | 2.5 | 5.9 | 4.2 |
| Dipropylene glycol | 0 | 19.5 | 26.0 | 19.5 | 32.5 |
| perfume | 45.5 | 13 | 19.5 | 0 | 0 |
| citric acid | | | qs pH 6 | | |
| water | | | qs | | |
| total surfactant | 19.5 | 32.5 | 19.5 | 45.5 | 32.5 |
| observations | Transparent low viscosity yellow liquid | Transparent low viscosity liquid | Transparent low viscosity liquid | Fluid No structured | Fluid No structured |

-continued

| Compositions (% wt.) | | | | | |
|---|---|---|---|---|---|
| G' at 1 Hz (Pa) | 0 | 0 | 0 | NA | NA |
| G" at 1 Hz (Pa) | NA | NA | NA | NA | NA |
| h zero shear (Pa · s) | NA | NA | NA | NA | NA |
| h 1 s$^{-1}$ shear (Pa · s) | NA | NA | NA | NA | NA |
| Lather volume (mL) | 310 | 820 | 550 | 875 | 930 |
| Lather density (g/cc) | 0.0446 | 0.0336 | 0.0381 | 0.0361 | 0.0241 |

| | COMP. EX. | | | | |
|---|---|---|---|---|---|
| | CEx. F | CEx. G | CEx. H | CEx. I | CEx. J |
| C13 Alkyl sulfate from Alcohol 1 | 28.3 | 32.6 | 34.0 | 45.2 | 39.6 |
| cocamidopropyl betaine | 4.2 | 4.9 | 5.0 | 6.8 | 5.9 |
| Dipropylene glycol | 0 | 15.6 | 16.2 | 0 | 16.2 |
| perfume | 32.5 | 9.4 | 9.7 | 13.0 | 3.2 |
| citric acid | | | qs pH 6 | | |
| water | | | qs | | |
| total surfactant | 32.5 | 37.5 | 39.0 | 52.0 | |
| observations | Transparent low viscosity liquid Phase separation@24 h | Translucent gel, phase separation | Phase separation | Stringy, rubbery gel but not rigid | Weak gel |
| G' at 1 Hz (Pa) | <1 | 18.8 | 35.7 | 590.1 | 16.5 |
| G" at 1 Hz (Pa) | NA | 8 | 12.4 | 124.4 | 6.2 |
| h zero shear (Pa · s) | NA | 638 | 1.53 | 21.47 | 0.5 |
| h 1 s$^{-1}$ shear (Pa · s) | NA | 2.02 | 3.03 | 77.65 | |
| Lather volume (mL) | 415 | | 790 | 890 | 910 |
| Lather density (g/cc) | 0.0323 | | 0.0350 | 0.0323 | 0.0345 |

It has been found that the compositions having an elastic modulus G' less than about 70 Pa do not comprise significant lamellar phase and tended to phase separate. For instance, Example E provided a stable gel having a stable lamellar phase as Example E did not phase separate, and had an elastic modulus G' of 72 Pa.

It has been evidenced as shown in FIG. 1 that the personal cleansing composition as defined herein comprising the surfactant that comprises a C13 alkyl sulfate anionic surfactant and a cosurfactant, needs to include from about 30% to about 50%, by weight of the composition, of a surfactant from about 4.5% to about 25%, by weight of the composition, of a perfume;

from about 3% to about 15%, by weight of the composition, of a hydric solvent; and water.

Then, the personal cleansing composition is structured and preferably may contain a lamellar phase and may be proximal to a microemulsion and/or may have a microemulsion phase in equilibrium with a lamellar phase.

Thus, the personal cleansing compositions may not have to necessarily be in a single microemulsion phase. The personal cleansing compositions may comprise two phases with one phase being a microemulsion and another one being a lamellar phase.

It follows that the personal cleansing composition itself does not necessarily need to be or dilute to a microemulsion, but part of the personal cleansing composition may be a microemulsion.

Improved Lather Stability

Some personal cleansing compositions may form microemulsions but perform poorly for lathering and hence cleaning, which are important features for consumers. Personal cleansing compositions which effectively deliver perfume as described above, can also have consumer acceptable lather properties.

In support of the need to focus on lather, we saw lather declines in lather volume in the stability test (albeit, volume not density) as a function of perfume concentration so it is appropriate to focus on how to make a better lather in formulas that have a high fragrance level. Lather can be measured in accordance with the Cylinder Method described hereinabove.

Personal cleansing compositions may have a lather volume of about 600 mL, preferably about 700 mL, or more, more preferably from 630 mL to 1050 mL.

Personal cleansing compositions may have a lather density of about 0.03 g/cc, about 0.04 g/cc, about 0.05 g/cc, 0.055 g/cc, 0.06 g/cc, 0.065 g/cc, or more.

Personal cleansing compositions may have a lather mass of about 20 g, about 25 g, about 30 g, about 35 g, about 40 g, about 45 g, or more.

Fragrance in personal cleansing compositions are known to act as a soil reducing foaming properties of the personal cleansing compositions. However, there is a need to provide personal cleansing compositions with a relatively high amount of perfume. The nature of the anionic surfactant has been assessed.

When the personal cleansing compositions comprise the C13 alkyl sulfate anionic surfactant as defined hereinabove, a denser lather is obtained, which is primarily a function of bubble elasticity resulting from improved packing at the interface compared to when the anionic surfactant is sodium trideceth-n sulfate (being either ST2S or ST3S).

Figure 2:
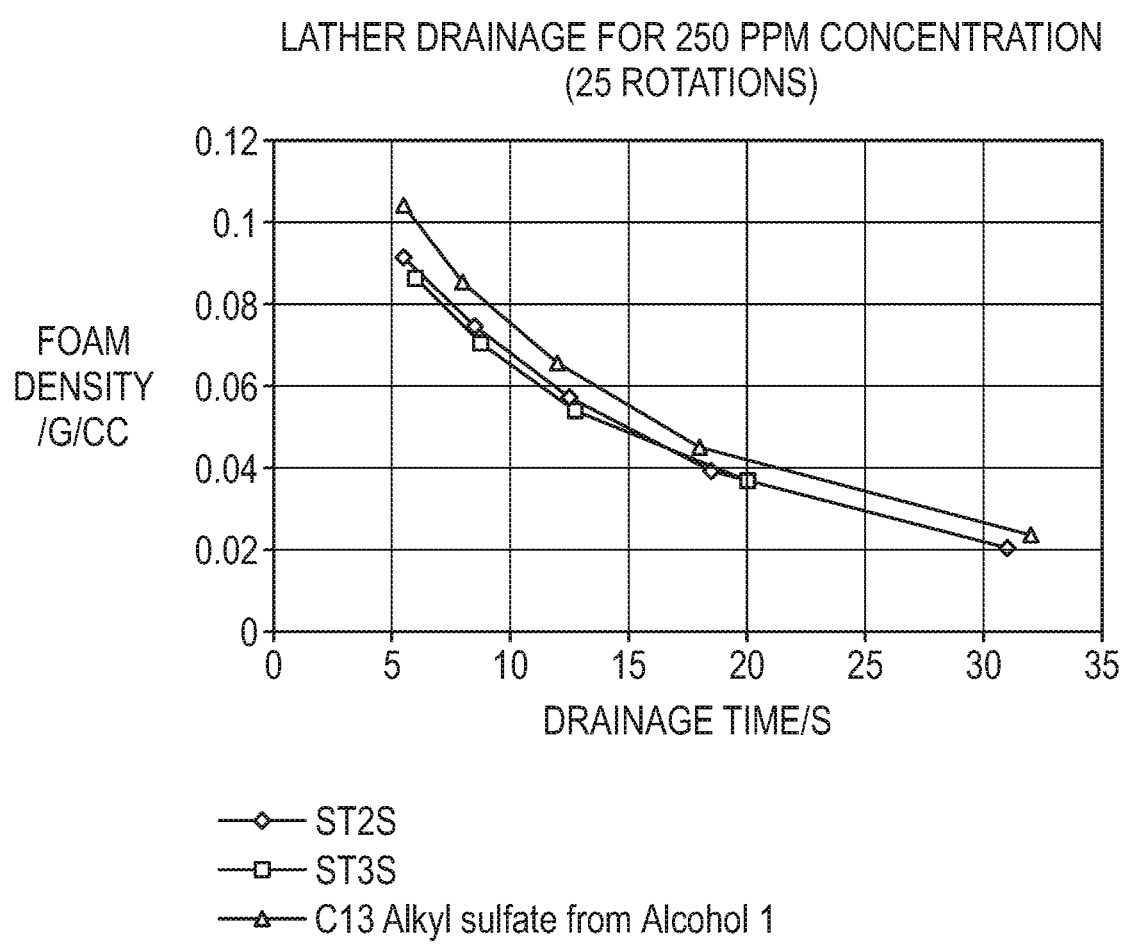
FIG. 2 and FIG. 3 show respectively the comparative data between different anionic surfactants in relation to the lather drainage for 250 ppm concentrations after 25 or 50 rotations.
Figure 3:
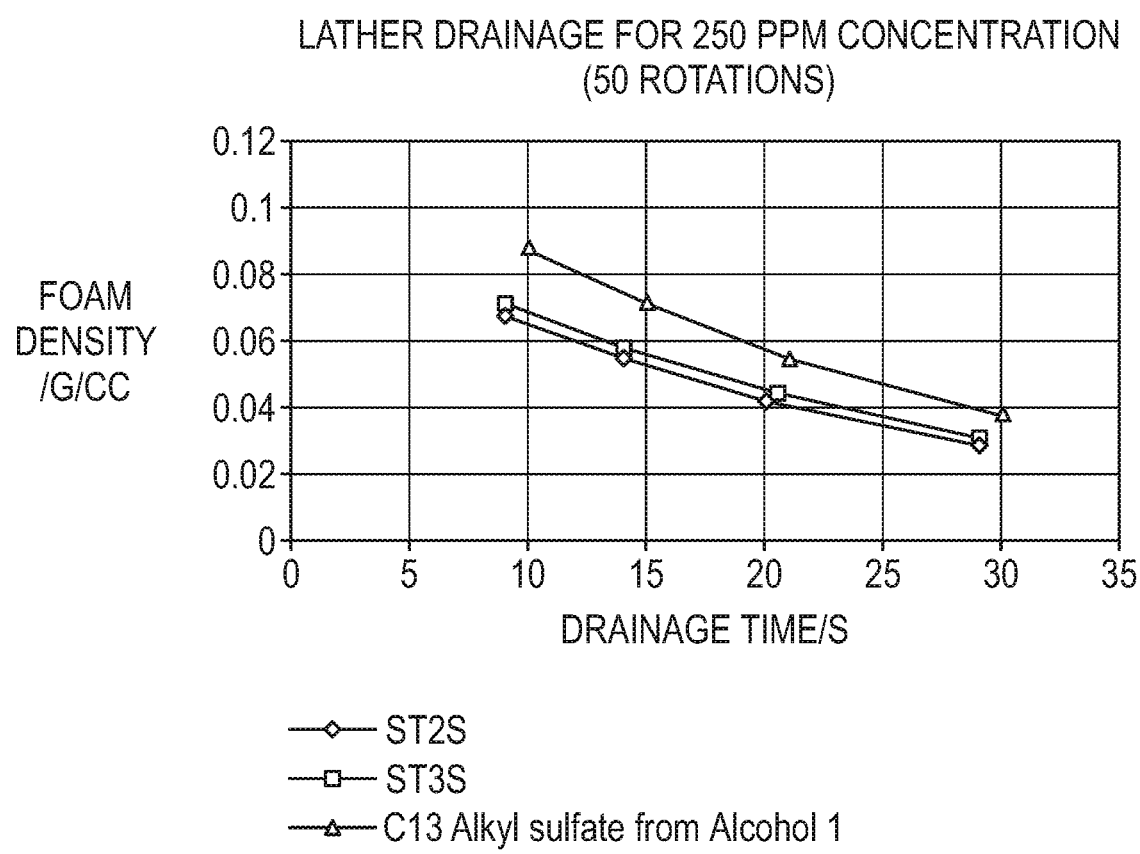

FIG. 2 and FIG. 3 show respectively the comparative data between different anionic surfactants in relation to the lather drainage for 250 ppm concentrations after 25 or 50 rotations. When the drainage time increases, the foam density decreased. However, when the personal cleansing composition comprises the C13 alkyl sulfate anionic surfactant as defined hereinabove, the foam density decreased less than for comparative anionic surfactants such as sodium trideceth-n sulfate (being either ST2S or ST3S).

The addition of C13 alkyl sulfate anionic surfactant as defined hereinabove in personal cleansing compositions can help to improve lather performance in a composition comprising a relatively high level of perfume, e.g. from about 4.5% to about 25%, preferably from about 7% to about 22%, more preferably from about 8% to about 20%, by weight of the composition, of a perfume.

Similar results have been obtained in terms of improved foam density in terms of better stability or better bubble elasticity for a surfactant system comprising the C13 alkyl sulfate anionic surfactant compared to both ST2S and ST3S when the cosurfactant, e.g. CAPB was included.

Figure 4:
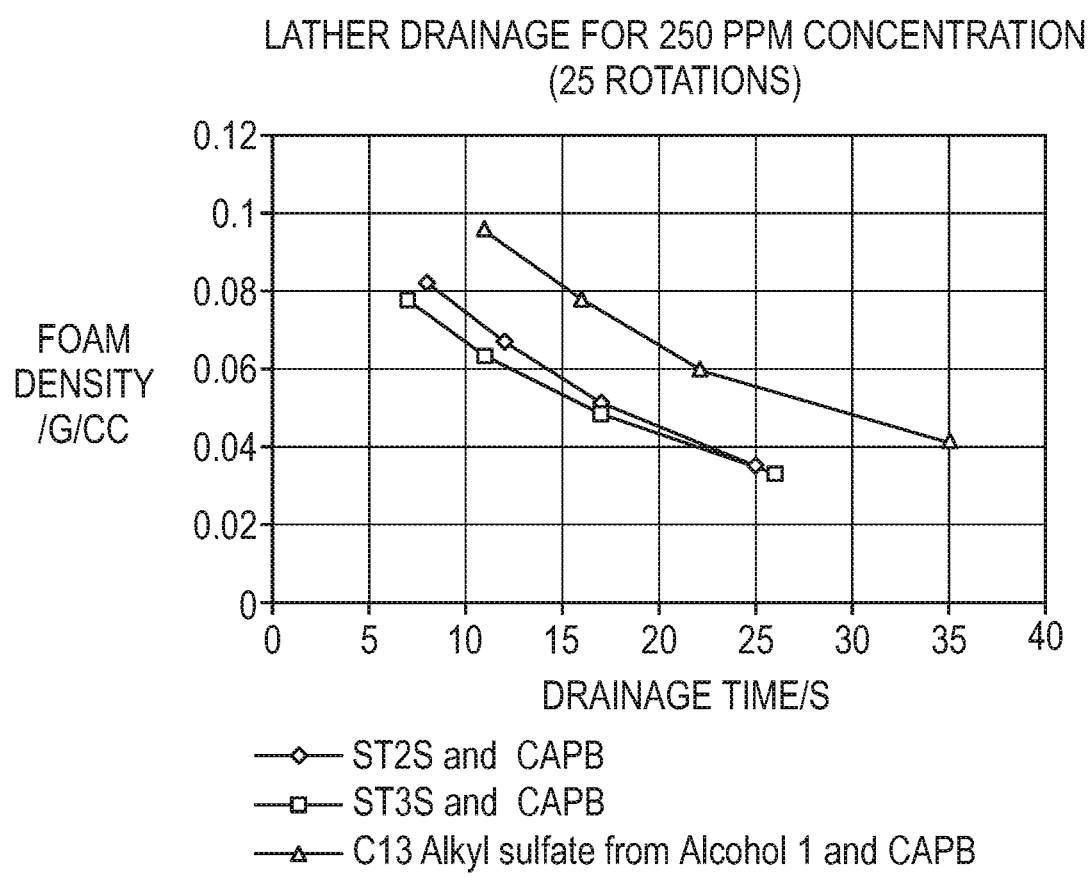
FIG. 4 and FIG. 5 show respectively the comparative data between different anionic surfactants with CAPB in relation to the lather drainage for 250 ppm concentrations after 25 or 50 rotations.
Figure 5:
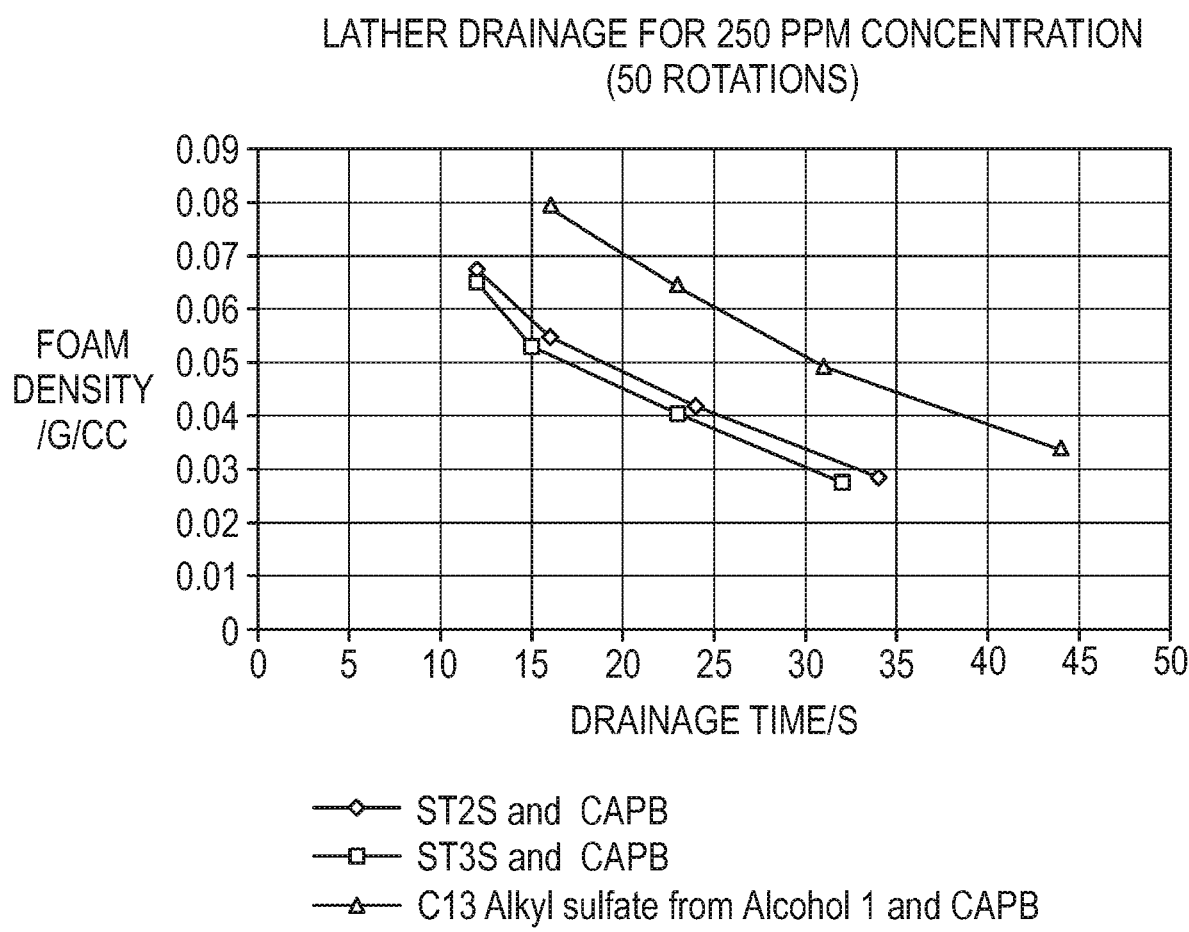

FIG. 4 and FIG. 5 show respectively the comparative data between different anionic surfactants with CAPB in relation to the lather drainage for 250 ppm concentrations after 25 or 50 rotations. Improved foam density has been obtained when the personal cleansing composition comprises the C13 alkyl sulfate anionic surfactant as defined hereinabove, over sodium trideceth-n sulfate (being either ST2S or ST3S).

Net, personal cleansing compositions comprising the C13 alkyl sulfate anionic surfactant as set out herein can help to improve the lather stability in terms of improved foam density during drainage.

The lather stability improvement appeared to grow even more when the ratio of the weight percent of C13 alkyl sulfate anionic surfactant to the weight percent of the cosurfactant is from 10:1 to 4:1, preferably from 9:1 to 5:1, more preferably from 8:1 to 6:1.

Miscibility by Optical Clarity—% Light Transmission at a Visible Wavelength of Light at 640 nm Certain analytical measures, such as neutron scattering, dynamic light scattering and optical light transmission, can be used as guides, when evaluating microemulsion phases. A spectrophotometer can be used to measure miscibility by optical clarity, by measuring % light transmission at a visible wavelength of light such as 640 nm.

Perfume miscibility of an anionic surfactant can be determined by mixing the anionic surfactant with a representative perfume or perfume molecule and measuring optical clarity. When the perfume-solvent mixture is less than fully transparent the mixture is no longer a molecular solution. The anionic surfactant is added until past the point of optical clarity, using a spectrophotometer to measure % Transmission for the mixture at an optical wavelength. Perfume miscibility is defined as the highest percentage of the anionic surfactant that can be added to a perfume, based on the weight of the two, which remains optically clear, i.e., generally about 90-100% T at 640 nm (minus a small amount of absorbance, but not scattering).

Figure 6:
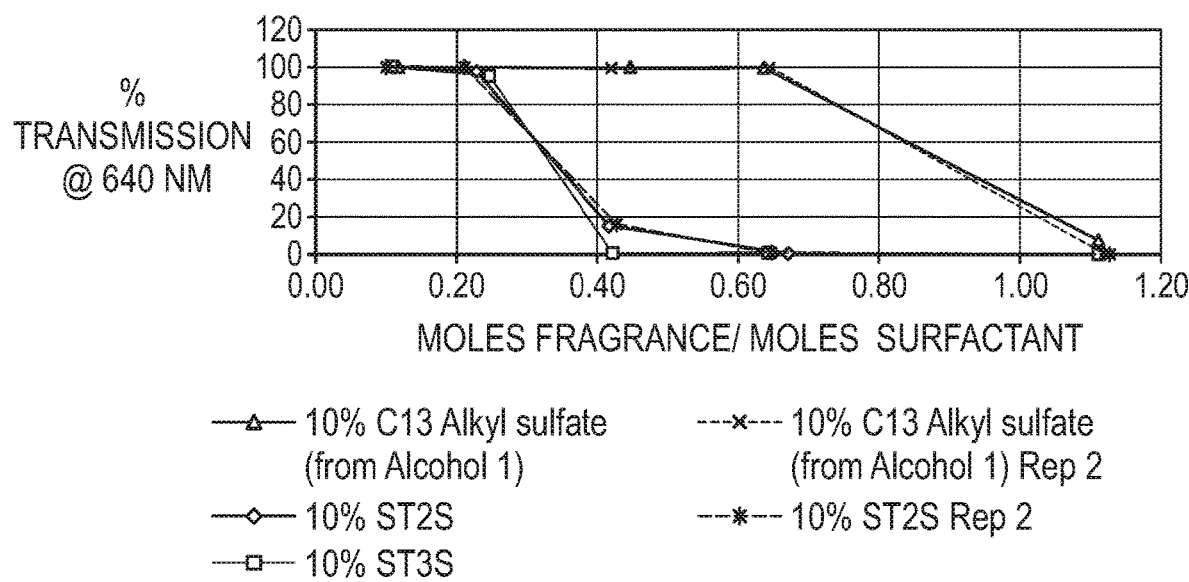
FIG. 6 is a graph showing the equilibrium solubility of a particular perfume in 10 wt. % anionic surfactant solutions at room temperature by % T at 640 nm to moles perfume/moles surfactant.

FIG. 6 is a graph showing the equilibrium solubility of a particular perfume at room temperature by % T at 640 nm to moles perfume/moles surfactant when modifying the nature of the anionic surfactant being a C13 alkyl sulfate anionic surfactant when comparing to sodium trideceth-n sulfate being either ST2S or ST3S.

As it can be seen, perfume miscibility has been improved when replacing the anionic surfactant being sodium trideceth-n sulfate (being either ST2S or ST3S) by a C13 alkyl sulfate anionic surfactant (C13 alkyl sulfate anionic surfactant from Alcohol 1).

Figure 7:
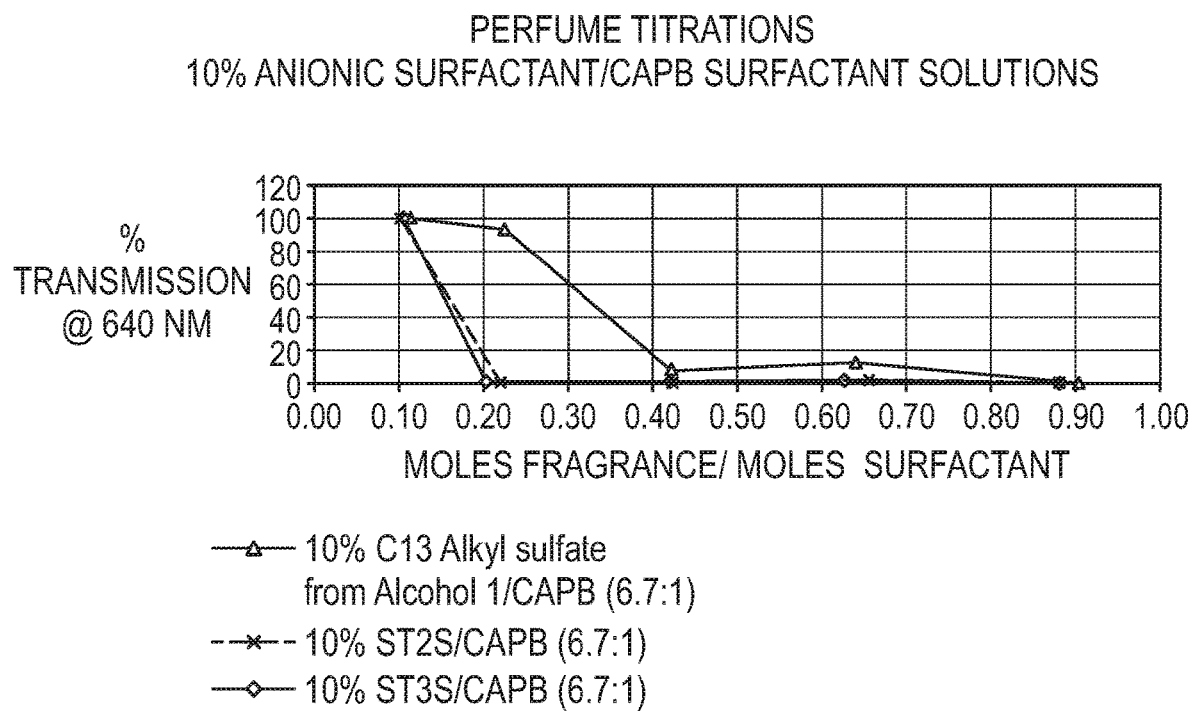
FIG. 7 is a graph showing the equilibrium solubility of a particular perfume in 10 wt. % anionic surfactant/CAPB surfactant solutions at room temperature by % T at 640 nm to moles perfume/moles surfactant.

FIG. 7 is a graph showing the equilibrium solubility of a particular perfume in 10% anionic surfactant/CAPB surfactant solutions at room temperature by % T at 640 nm to moles perfume/moles surfactant.

Similar observations for perfume solubility have been found in C13 alkyl sulfate anionic surfactant/cocamidopropyl betaine (CAPB) mixtures over sodium trideceth-n sulfate (being either ST2S or ST3S)/CAPB. C13 alkyl sulfate anionic surfactant/CAPB has higher capacity to solubilize fragrance versus ST2S/CAPB and ST3S/CAPB.

The C13 alkyl sulfate anionic surfactant as defined hereinabove has a higher capacity to solubilize fragrance over sodium trideceth-n sulfate being either ST2S or ST3S.

Perfume Headspace Abundance During Dilution

When the microemulsion phase is present, increased bloom and/or relative bloom can be demonstrated by measuring the relative abundance of perfume in the headspace over the composition or comparative composition using the Perfume Headspace Abundance During Dilution Method (PHADD), which utilizes solid phase microextraction GCMS (SPME-GCMS) to collect and evaluate perfume molecules (PRM) in the headspace over a neat composition and through stepwise aqueous dilutions. Results can be compared to a control micelle composition CEx. 0 using the same perfume.

Figure 8:
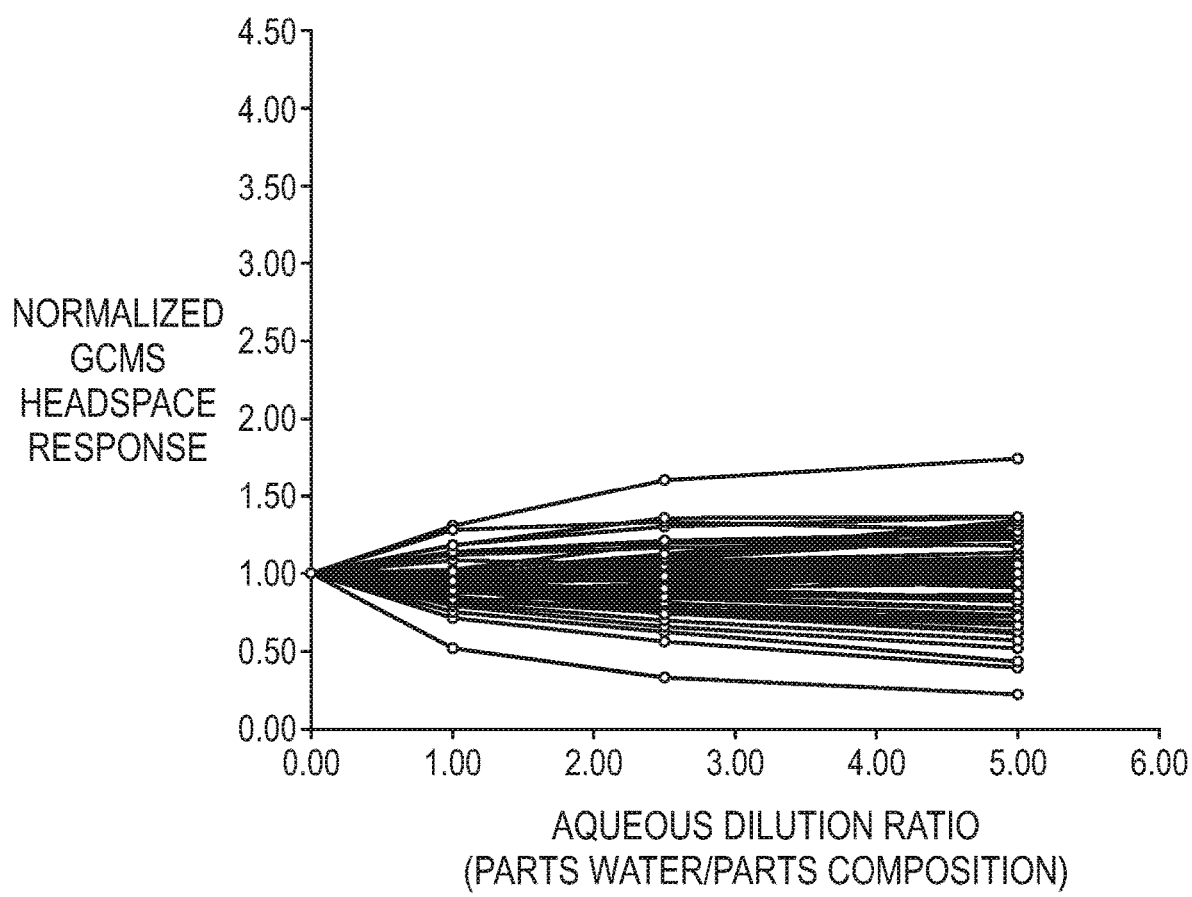
FIG. 8 is a normalized GCMS Headspace response for a comparative personal cleansing composition not within the scope of the invention.
Figure 9:
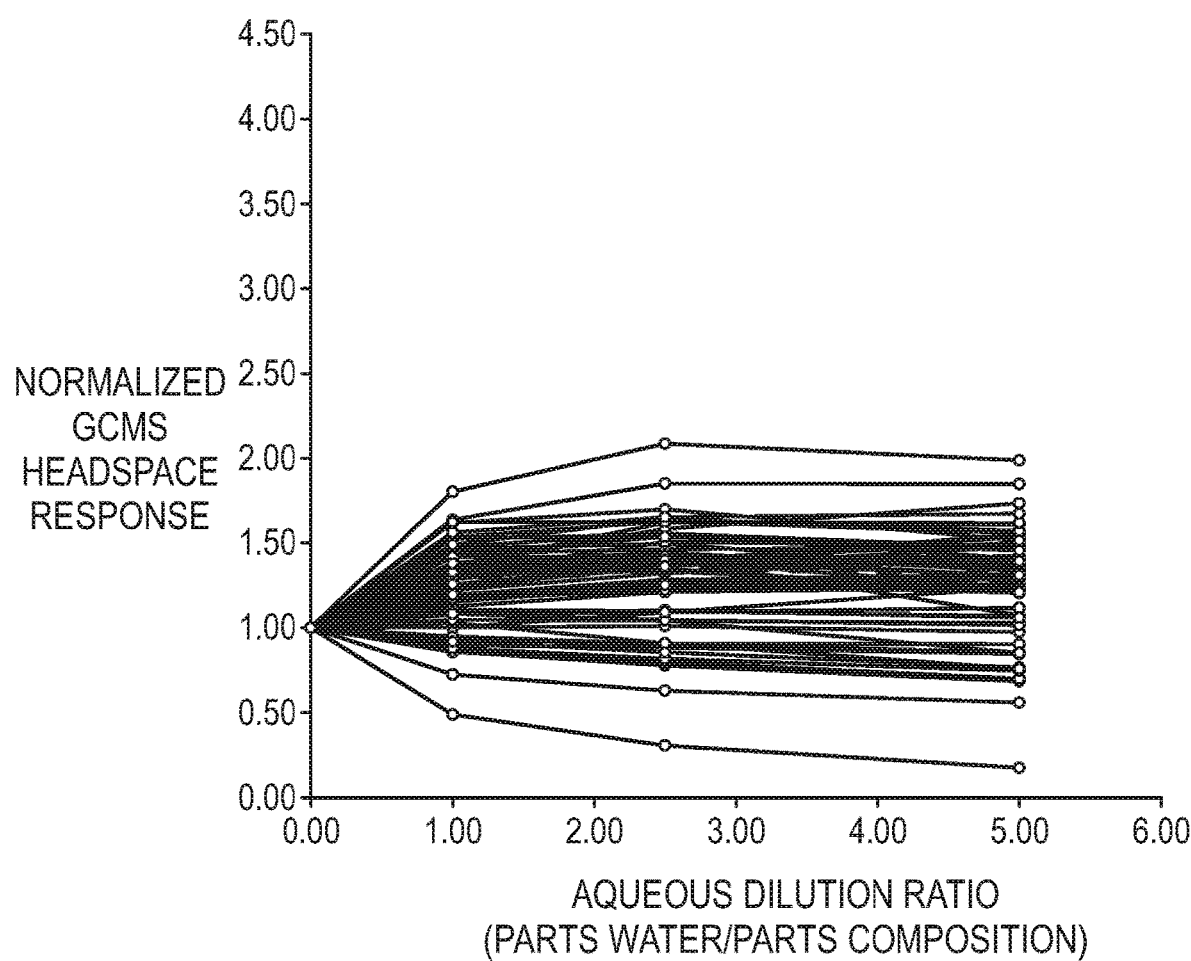
FIG. 9 is a normalized GCMS Headspace response for a personal cleansing composition according to one or more aspects.

FIG. 8 is a normalized GCMS Headspace response for a comparative personal cleansing composition CEx. 0 not within the scope of the invention. FIG. 9 is a normalized GCMS Headspace response for a personal cleansing composition Ex. 0 according to one or more aspects.

Both FIGS. 8-9 show headspace for a mixture of perfume raw materials (PRM) for the compositions tested below. Each curve represents a PRM (this can also be color coded) and are the same across FIGS. 8-9, but are not labeled. The median response may be shown on each graph as a thicker dotted black line.

The personal cleansing composition Ex. 0 comprises 36.75 wt. % of C13 Alkyl sulfate (from Alcohol 1), 5.5 wt. % of cocamidopropyl betaine, 13 wt. % dipropylene glycol and 9.75 wt. % of the same fragrance comprising a mixture of perfume raw materials as in Ex. 0. The personal cleansing composition may include a microemulsion, that is able to lead to a perfume microemulsion. Upon dilution, more and more microemulsions will be obtained.

The comparative personal cleansing composition CEx. 0 includes 9 wt. % of sodium laureth-1 sulfate, 1 wt. % cocamidopropylbetaine and 1 wt. % of the same fragrance. The comparative personal cleansing compositions does not comprise a microemulsion and only provide micelles.

A perfume raw material can be characterized by its octanol/water partitioning coefficient (P). The octanol/water partitioning coefficient of a perfume raw material is the ratio between its equilibrium concentrations in octanol and in water.

The perfume raw materials (PRM) of the fragrance can be classified in three groups with:

a relatively low logP group with logP<2.5 as blooming PRM;

a relatively medium logP with 2.5<logP<4.25 as medium blooming PRM; and a relatively high log P with logP>4.25 as heavy blooming PRM.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume raw material.

As shown in FIG. 8, for the comparative personal cleansing composition CEx. 0, during dilution, the expanded aqueous phase dilutes PRM with low logP<2.5, leading to decreases in headspace abundance due to the added solvent water. The departure of low logP PRM from the micelles removes their solvent influence on remaining PRM, such that those increase in the headspace by up to about 50%. These effects are known and relatively muted in terms of consumer impact.

As shown in FIG. 9, for the personal cleansing composition Ex. 0 expected to dilute into microemulsions, headspace concentration of many PRM increase, some PRM by 2-fold to up to 4-fold. This effect is due to selective movement of PRM into the microemulsion core, supporting the mechanism of microemulsion fragrance bloom and skin delivery.

Figure 10:
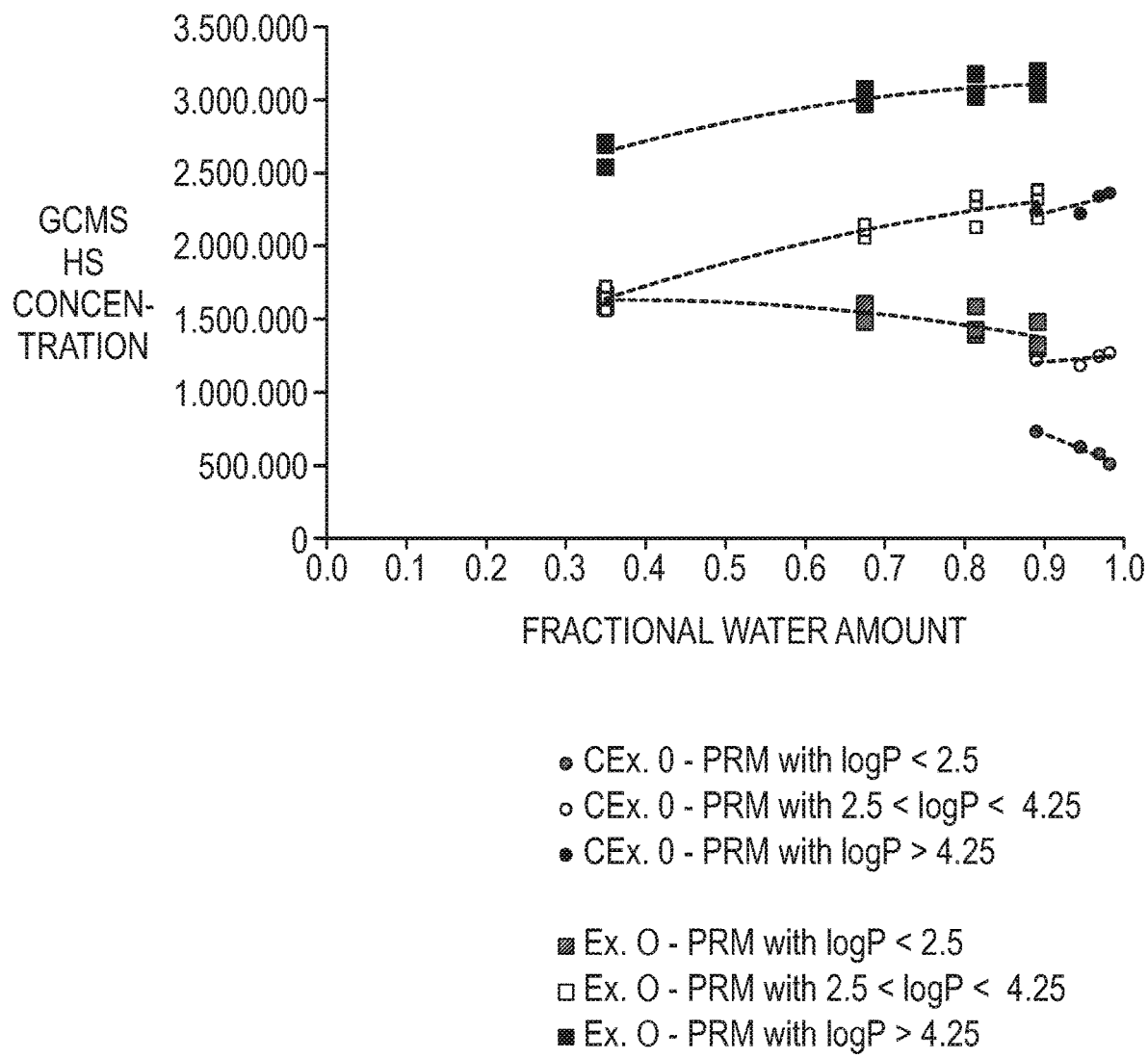
FIG. 10 is Headspace response for perfume raw materials as grouped by logP, when including in a personal cleansing composition (squares) versus a comparative personal cleansing composition (circles).

FIG. 10 is Headspace response for perfume raw materials as grouped by logP, when including in a personal cleansing composition (squares) versus a comparative personal cleansing composition (circles). In FIG. 10, the personal cleansing composition within the scope of the invention starts at higher headspace concentration due to higher fragrance levels, and Headspace response increases substantially for midrange and high log P perfume raw materials due to formation of a microemulsion phase on dilution.

In FIG. 10, a single diagram is provided by grouping the perfume raw materials (PRM) of the fragrance into blooming (logP<2.5), midrange (2.5<logP<4.25) and heavy (logP>4.25), and plotting the personal cleansing composition of Ex. 0 together to compare to the comparative personal cleansing compositions CEx. 0.

As shown in FIG. 10, as compositions are diluted, fractional water amount increases, moving from left to right in the diagram as a function of increasing dilution. The less hydrophobic PRM decrease in both compositions due to increased solvent water. For midrange PRM the micelle performance is flat with dilution but headspace increases by about 50% for the composition within the scope of the invention. This would be expected to result in a strong shower bloom effect, added on top of the already high starting point (which is largely due to the microemulsion personal cleansing composition holding more perfume than a micelle is capable of). For heavy, more residual scented PRM, there is a slight increase as indicated above for the composition Ex. 0 and about 25% increase in the overall group for the compositions within the scope of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:
   (i) about 30% to about 50%, by weight of the composition, of a surfactant, wherein the surfactant comprises a C13 alkyl sulfate anionic surfactant and a cosurfactant, wherein the C13 alkyl sulfate anionic surfactant consists of:
      (a) a linear C13 alkyl sulfate; wherein the C13 alkyl sulfate anionic surfactant consists of less than about 40% by weight of the C13 alkyl sulfate anionic surfactant of the linear C13 alkyl sulfate, and
      (b) more than about 60% by weight of the C13 alkyl sulfate anionic surfactant of a 2-branched C13 alkyl sulfate anionic surfactant, wherein the 2-branched C13 alkyl sulfate anionic surfactant comprises:
         about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and
      (c) less than about 5% by weight of the C13 alkyl sulfate anionic surfactant of other branched C13 alkyl sulfate anionic surfactant,
      wherein a, b and c add up to about 100% by weight of the C13 alkyl sulfate anionic surfactant;
   (ii) about 4.5% to about 25%, by weight of the composition, of a perfume;
   (iii) about 3% to about 15%, by weight of the composition, of a hydric solvent; and
   (iv) water;
      wherein the composition is structured; and
      wherein the personal cleansing composition comprises a viscosity at about 0.10 l/sec of from about 10 Pa·s to about 1200 Pa·s.

2. The personal cleansing composition of claim 1, wherein the personal cleansing composition is a stable gel and has an elastic modulus G' at 1 Hz of about 70 Pa to about 2500 Pa according to the G' and G" Test Method.

3. The personal cleansing composition according to claim 1, wherein the C13 alkyl sulfate anionic surfactant consists of:
   (i) less than about 30%, by weight of the C13 alkyl sulfate anionic surfactant, of the linear C13 alkyl sulfate;
   (ii) more than about 70%, by weight of the C13 alkyl sulfate anionic surfactant, of the 2-branched C13 alkyl sulfate anionic surfactant; and
   (iii) less than about 3%, by weight of the C13 alkyl sulfate anionic surfactant of other branched C13 alkyl sulfate anionic surfactants.

4. The personal cleansing composition according to claim 1, wherein the 2-branched C13 alkyl sulfate anionic surfactant comprises:
  (i) less than about 20%, by weight of the 2-branched C13 alkyl sulfate anionic surfactant, of 2-pentyl octyl sulfate anionic surfactant; and
  (ii) more than about 30%, by weight of the 2-branched C13 alkyl sulfate anionic surfactant, of 2-methyl dodecyl sulfate anionic surfactant.

5. The personal cleansing composition according to claim 1, wherein the personal cleansing composition is substantially free or free of alkoxylated anionic sulfate surfactant.

6. The personal cleansing composition according to claim 1, wherein the weight percent of perfume is about 2% to about 90%, by weight of the surfactant.

7. The personal cleansing composition according to claim 1, wherein the weight percent of the hydric solvent is about 5% to about 35%, by weight of the surfactant.

8. The personal cleansing composition according to claim 1, wherein the cosurfactant is present at about 2.5% to about 5%, by weight of the composition.

9. The personal cleansing composition of claim 8, wherein the cosurfactant is chosen from a zwitterionic surfactant, an amphoteric surfactant, a nonionic surfactant, or mixtures thereof.

10. The personal cleansing composition according to claim 8, wherein the ratio of the weight percent of C13 alkyl sulfate anionic surfactant to the weight percent of the cosurfactant is 20:1 to 4:1.

11. The personal cleansing composition according to claim 1, wherein the composition comprises about 5% to about 62.5%, by weight of the composition, of water.

12. The personal cleansing composition according to claim 1, wherein the composition has a microemulsion phase.

13. The personal cleansing composition according to claim 12, wherein the microemulsion phase is in equilibrium with a lamellar phase.

14. The personal cleansing comprising according to claim 1, wherein the hydric solvent is a glycol comprising 3 to 12 carbon atoms or a glycol ether comprising 4 to 12 carbon atoms.

15. The personal cleansing comprising according to claim 14, wherein the hydric solvent is a glycol chosen from hexylene glycol, butylene glycol, pentylene glycol, heptylene glycol, propylene glycol, or mixtures thereof.

16. The personal cleansing composition according to claim 14, wherein the hydric solvent is a glycol ether chosen from dipropylene glycol, diethylene glycol, dibutylene glycol, or mixtures thereof.

17. The personal cleansing comprising according to claim 1, wherein the composition is not a ringing gel.

18. The personal cleansing comprising according to claim 1, wherein at least a portion of the composition becomes a microemulsion upon dilution with water of about 3:1 by weight (water:composition) to about 10:1 by weight (water:composition).

19. A personal cleansing composition comprising:
  (i) a surfactant, wherein the surfactant comprises an alkyl sulfate anionic surfactant and a cosurfactant, wherein the alkyl sulfate anionic surfactant consists of:
    (a) a linear alkyl sulfate; wherein the alkyl sulfate anionic surfactant consists of less than about 40% by weight of the alkyl sulfate anionic surfactant of the linear alkyl sulfate, and
    (b) more than about 60% by weight of the alkyl sulfate anionic surfactant of a 2-branched C13 alkyl sulfate anionic surfactant, wherein the 2-branched C13 alkyl sulfate anionic surfactant comprises:
      about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant;
    (c) optionally one or more other branched alkyl sulfate anionic surfactants,
      wherein a, b and c add up to about 100% by weight of the alkyl sulfate anionic surfactant;
      wherein the surfactant is substantially free of ethoxylated anionic sulfate surfactants,
  (ii) a perfume at a weight ratio perfume: surfactant of at least about 1:10;
  (iii) a hydric solvent at a weight ratio hydric solvent: surfactant of at least about 2:9, between about 25% to about 50% water by weight of the composition;
    wherein the personal cleansing composition comprises a viscosity at about 0.10 l/sec of from about 10 Pa·s to about 1200 Pa·s;
    wherein the personal cleansing composition has an elastic modulus G' at 1 Hz from about 70 Pa to about 2500 Pa according to the G' and G" Test Method as disclosed herein.

20. A method of providing similar or enhanced in-vitro bloom or fragrance skin deposition of a rinse-off microemulsion cleansing composition, comprising, providing a personal cleansing composition comprising a perfume and a synergistic combination of a C13 alkyl sulfate anionic surfactant and a hydric solvent, comprising:
  (i) about 30% to about 50%, by weight of the composition, of a surfactant, wherein the surfactant comprises a C13 alkyl sulfate anionic surfactant and a cosurfactant, wherein the C13 alkyl sulfate anionic surfactant consists of:
    (a) a linear C13 alkyl sulfate; wherein the C13 alkyl sulfate anionic surfactant consists of less than about 40% by weight of the C13 alkyl sulfate anionic surfactant of the linear C13 alkyl sulfate, and
    (b) more than about 60% by weight of the C13 alkyl sulfate anionic surfactant of a 2-branched C13 alkyl sulfate anionic surfactant, wherein the 2-branched C13 alkyl sulfate anionic surfactant comprises:
      about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant, and
    (c) less than about 5% by weight of other branched C13 alkyl sulfate anionic surfactant,
      wherein a, b and c add up to about 100% by weight of the C13 alkyl sulfate anionic surfactant;
  (ii) about 4.5% to about 25%, by weight of the composition, of a perfume;
  (iii) about 3% to about 15%, by weight of the composition, of a hydric solvent; and water to obtain a personal cleansing composition containing a microemulsion then diluting diluting the personal cleansing composition with water at a weight ratio water:composition from about 2:1 to about 10:1, to form a rinse-off microemulsion cleansing composition comprising a micoemulsion phase comprising a portion of the perfume.

\* \* \* \* \*